United States Patent
Arai et al.

(10) Patent No.: US 9,246,110 B2
(45) Date of Patent: Jan. 26, 2016

(54) ORGANIC MATERIAL AND PHOTOELECTRIC CONVERSION ELEMENT

(71) Applicants: Ryota Arai, Shizuoka (JP); Yu Hidaka, Fukuoka (JP); Woong Shin, Fukuoka (JP); Chihaya Adachi, Fukuoka (JP); Takuma Yasuda, Fukuoka (JP)

(72) Inventors: Ryota Arai, Shizuoka (JP); Yu Hidaka, Fukuoka (JP); Woong Shin, Fukuoka (JP); Chihaya Adachi, Fukuoka (JP); Takuma Yasuda, Fukuoka (JP)

(73) Assignees: RICOH COMPANY, LTD., Tokyo (JP); KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 0 days.

(21) Appl. No.: 14/669,318

(22) Filed: Mar. 26, 2015

(65) Prior Publication Data
US 2015/0280142 A1 Oct. 1, 2015

(30) Foreign Application Priority Data

Apr. 1, 2014 (JP) ................................. 2014-075301

(51) Int. Cl.
*H01G 9/20* (2006.01)
*H01L 51/00* (2006.01)
(Continued)

(52) U.S. Cl.
CPC .......... *H01L 51/0074* (2013.01); *C07D 495/04* (2013.01); *H01L 51/0037* (2013.01);
(Continued)

(58) Field of Classification Search
CPC .................................................. H01G 9/2059
USPC ......................................................... 136/263
See application file for complete search history.

(56) References Cited

U.S. PATENT DOCUMENTS 6,384,321 B1 * 5/2002 Mikoshiba ........... H01G 9/2004
136/256
(Continued)

FOREIGN PATENT DOCUMENTS

JP 2013-102148 5/2013
JP 2014-177426 9/2014

OTHER PUBLICATIONS

Chem. Mater., 2013, 25 (12), 2549-2556.
(Continued)

Primary Examiner — Golam Mowla
(74) Attorney, Agent, or Firm — Cooper & Dunham LLP

(57) ABSTRACT

An organic material represented by the following General Formula (1):

<General Formula (1)>

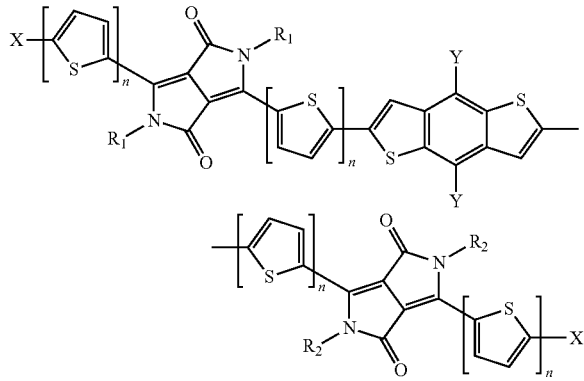

where in the General Formula (1), $R_1$ and $R_2$, which may be identical to or different from each other, each represent an alkyl group having 4 to 24 carbon atoms, X represents a substituted or unsubstituted aromatic hydrocarbon group, Y represents an aromatic hydrocarbon group, an alkoxyl group, or an alkyl group, which may be substituted with a substituent, and n represents an integer of 1 to 3.

11 Claims, 2 Drawing Sheets

(51) Int. Cl.
*C07D 495/04* (2006.01)
*H01L 51/44* (2006.01)

(52) U.S. Cl.
CPC ........ *H01L51/0046* (2013.01); *H01L 51/0068* (2013.01); *H01L 51/0072* (2013.01); *H01L 51/442* (2013.01)

(56) References Cited

U.S. PATENT DOCUMENTS

| | | | | |
|---|---|---|---|---|
| 6,407,330 B1 * | 6/2002 | Lindsey | ................ | B82Y 30/00 136/252 |
| 8,558,109 B2 * | 10/2013 | Wigglesworth | ..... | H01L 51/0036 136/263 |
| 8,575,477 B1 * | 11/2013 | Coggan | .............. | H01L 51/0036 136/263 |
| 2002/0055046 A1 * | 5/2002 | Ono | ..................... | H01G 9/2009 429/324 |
| 2002/0082422 A1 * | 6/2002 | Paidi | .................... | C07D 213/79 546/2 |
| 2003/0013008 A1 * | 1/2003 | Ono | ..................... | H01G 9/2009 429/111 |
| 2008/0206890 A1 * | 8/2008 | Burstyn | ................. | C07F 1/005 436/525 |
| 2010/0326525 A1 * | 12/2010 | Nguyen | ................. | B82Y 10/00 136/263 |
| 2011/0114184 A1 * | 5/2011 | Brown | ................. | C07D 487/04 136/263 |
| 2013/0098449 A1 * | 4/2013 | Okubo | ................. | B82Y 10/00 136/263 |
| 2014/0264184 A1 | 9/2014 | Arai et al. | | |

OTHER PUBLICATIONS

ACS Appl. Mater. Interfaces, 2013, 5 (6), 2033-2039.

* cited by examiner

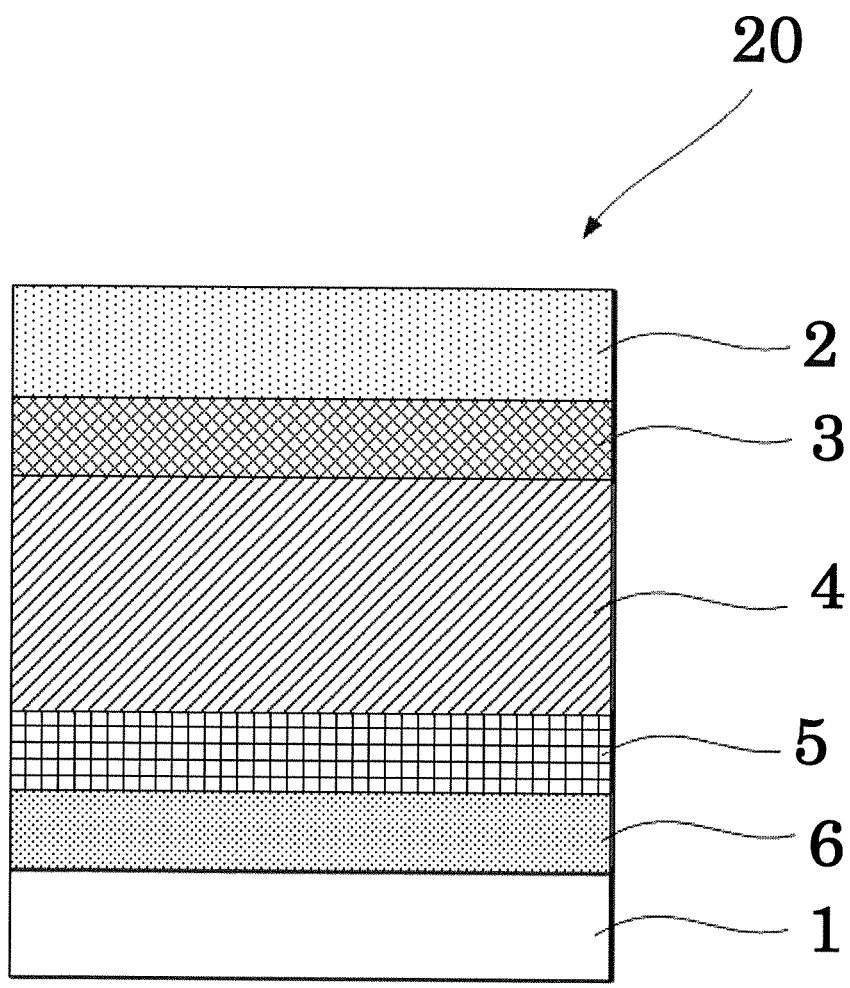

ORGANIC MATERIAL AND PHOTOELECTRIC CONVERSION ELEMENT

BACKGROUND OF THE INVENTION

1. Field of the Invention

The present invention relates to organic materials and a photoelectric conversion element using the same.

2. Description of the Related Art

In recent years, importance of solar cells has been increasing as an alternative energy to fossil fuel and as a measure against global warming. However, existing solar cells typified by silicon solar cells are costly at present, which is a factor of preventing them from being widely used. Therefore, research and development on various low-cost solar cells have been advancing. In particular, one example thereof is an organic thin film solar cell. The organic thin film solar cell is lightweight, low-priced, and easily enlarged in its surface area. Thus, expectations for practical applications have been increased. However, the photoelectric conversion efficiency of the organic thin film solar cell is still ½ or less that of the silicone-based solar cells.

A photoelectric conversion layer of the organic thin film solar cell includes a p-type semiconductor and a n-type semiconductor. Excitons generated in the p-type semiconductor and/or the n-type semiconductor by light absorption are dispersed to a pn interface, and then, are separated into electrons and holes at the pn interface. Next, the separated electrons and holes are each transferred to a trapping electrode, and are taken out to an external circuit. However, organic materials have an exciton diffusion length of about only several nanometers, and a diffusion length of the separated electric charge is also much inferior to silicon or the like although it cannot flatly be said since the diffusion length is greatly influenced by its crystalline state.

A bulk heterojunction structure which is disorderly formed by mixing the p-type semiconductor material and the n-type semiconductor material, or a regular bulk heterojunction structure which has order to ensure a charge transport path, or the like is one of the structures which solve the problems such as a diffusion length of the exciton and charge transportation, and are indispensable for improvement in photoelectric conversion efficiency. In the bulk heterojunction structure, the pn interface is disposed within a range of several nanometers from a place where the excitons are generated, which improves exciton separation efficiency. Moreover, by ensuring the charge transport path, the electric charge can be transferred to each of the electrode without binding them each other during transportation, and thus, a large amount of electrical current can be taken out to an external circuit.

Regarding organic materials mainly used at present, a lot of conjugated polymers have been reported as the p-type semiconductor material. The conjugated polymers easily form a bulk heterojunction structure, which is excellent in charge separation ability and charge transport ability. However, the conjugated polymers have a problem in that it is difficult to obtain high open circuit voltage since their ionization potential, which is a material property correlated to the open end voltage, is low due to extended conjugation thereof. Moreover, they are polymers and have a molecular weight distribution, which causes a problem in that stable materials are difficult to obtain during production.

In order to solve the problems, organic, low-molecular-weight, p-type semiconductor materials that can be formed into an element by a coating method, which needs no vacuum process, have been reported.

The present inventor has previously reported a photoelectric conversion element containing a diketopyrrolopyrrole derivative that is a low-molecular-weight organic material and has a certain structure (refer to "Chem. Mater., 2013, 25 (12), 2549-2556"). Moreover, the present inventor has also reported a diketopyrrolopyrrole derivative containing a benzodithiophene derivative (refer to "ACS Appl. Mater. Interfaces, 2013, 5 (6), 2033-2039").

However, the former has a high ionization potential and a high open circuit voltage, but it can absorb light of short wavelengths, and thus is insufficient in photoelectric conversion efficiency. Meanwhile, the latter can absorb light of relatively longer wavelengths, but it is poor in aggregated structure responsible for charge transport path and charge separation, and thus is still insufficient in photoelectric conversion efficiency.

Thus, it has been desired to provide a novel organic material which has a high open circuit voltage, can absorb light of a wide wavelength range, and is excellent in charge transport ability, when it is applied to an organic thin film solar cell system.

BRIEF DESCRIPTION OF THE DRAWINGS

An object of the present invention is to provide a novel organic material which has a high open circuit voltage, can absorb light of a wide wavelength range, and is excellent in charge transport ability, when it is applied to an organic thin film solar cell system.

An organic material of the present invention serving as a mean for solving the problems is represented by the following General Formula (1).

<General Formula (1)>

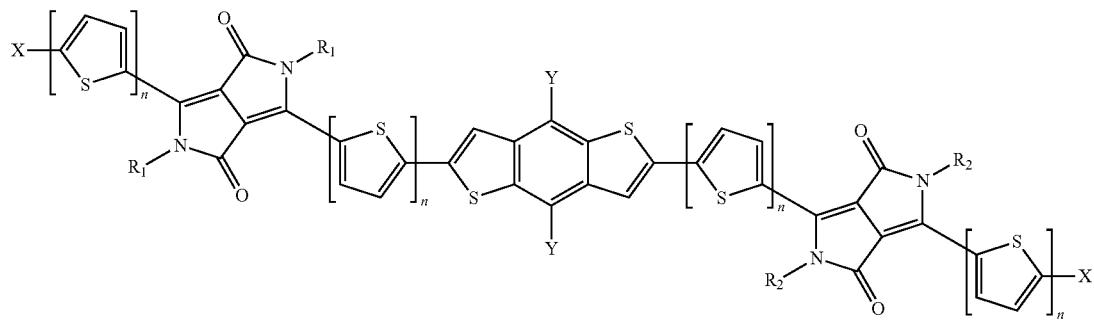

Figure 1:
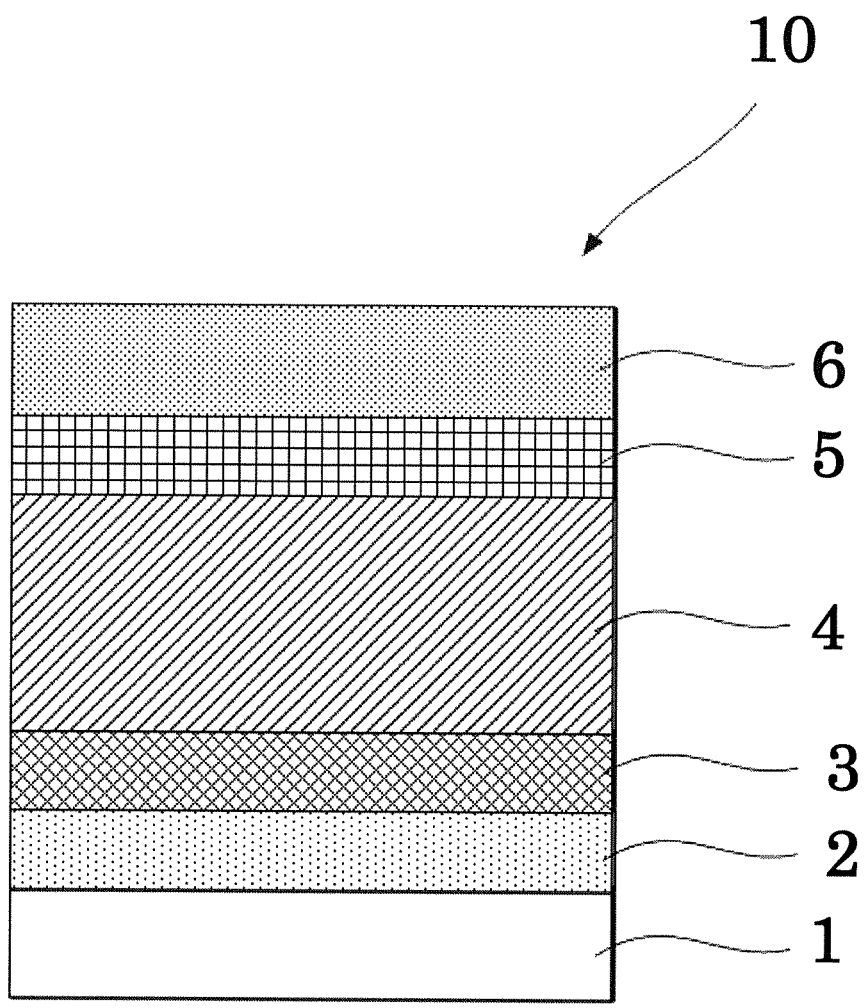

In the General Formula (1), $R_1$ and $R_2$, which may be identical to or different from each other, each represent an alkyl group having 4 to 24 carbon atoms. X represents a substituted or unsubstituted aromatic hydrocarbon group. Y represents an aromatic hydrocarbon group, an alkoxyl group, or an alkyl group, which may be substituted with a substituent. n represents an integer of 1 to 3.

The present invention can provide a novel organic material which has a high open circuit voltage, can absorb light of a wide wavelength range, and is excellent in charge transport ability when it is applied to an organic thin film solar cell system. The novel organic material can solve the existing problems.

BRIEF DESCRIPTION OF THE DRAWINGS

FIG. 1 is a schematic view of one example of a normal-type photoelectric conversion element of the present invention.

FIG. 2 is a schematic view of one example of an inverse-type photoelectric conversion element of the present invention.

DETAILED DESCRIPTION OF THE INVENTION

Organic Material

An organic material of the present invention is represented by the following General Formula (1).

groups and heterocyclic aromatic hydrocarbon groups such as a phenyl group, a naphthyl group, an anthryl group, a fluorenyl group, a thienyl group, and a 3-thiazolyl group. Among them, a phenyl group and a thienyl group are preferable.

Examples of the substituent in X include an alkyl group. The alkyl group may be a straight chain or a branched chain, but the straight chain alkyl is preferable from the viewpoint of improving an aggregated structure. Examples of the alkyl group include those similar to the aforementioned alkyl groups.

In the General Formula (1), Y represents an aromatic hydrocarbon group, an alkoxyl group, or an alkyl group, and is preferably an aromatic hydrocarbon group from the viewpoint of improving an aggregated structure related to charge transportation.

The aromatic hydrocarbon group in Y may be substituted or unsubstituted. Examples thereof include aromatic hydrocarbon groups and heterocyclic aromatic hydrocarbon groups such as a phenyl group, a naphthyl group, an anthryl group, a fluorenyl group, a thienyl group, and a 3-thiazolyl group. Among them, a phenyl group and a thienyl group are preferable.

A substituent in the aromatic hydrocarbon group in Y may be an alkyl group or an alkoxy group. The alkyl group may be a straight chain or a branched chain, but the branched chain alkyl group is preferable from the viewpoint of improving solubility. Examples thereof include a 2-ethylhexyl group, a 2-hexyldecyl group, and a 2-decyldodecyl group.

Examples of the alkoxy group include a methoxy group, an ethoxy group, and a butoxy group. The alkoxy group may be <General Formula (1)>

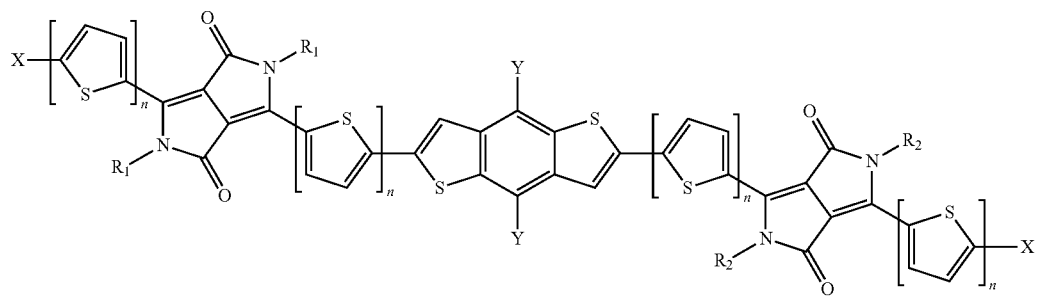

In the General Formula (1), $R_1$ and $R_2$, which may be identical to or different from each other, each represent an alkyl group having 4 to 24 carbon atoms. The alkyl group having 4 to 24 carbon atoms may be a straight chain or a branched chain, but the branched chain is preferable from the viewpoint of improving solubility. Examples thereof include a n-hexyl group, a n-octyl group, a n-dodecyl group, a n-octadecyl group, a 2-ethylhexyl group, a 2-hexyldecyl group, and a 2-decyldodecyl group. Among them, a 2-ethylhexyl group and a 2-hexyldecyl group are preferable.

In the General Formula (1), X represents a substituted or unsubstituted aromatic hydrocarbon group. Examples of the aromatic hydrocarbon group include aromatic hydrocarbon a straight chain or a branched chain, but the branched alkoxy group is preferable from the viewpoint of improving solubility. Examples thereof include a 2-ethylhexyloxy group, a 2-hexyldecyloxy group, and a 2-decyldodecyl group.

In the General Formula (1), n represents an integer of 1 to 3, and is preferably 1 because ionization potential is maintained to be deep.

The organic material of the present invention is preferably a compound represented by the following General Formula (2) because it develops an aggregated structure in order to generate electric charges, and deeply maintains an ionization potential.

<General Formula (2)>

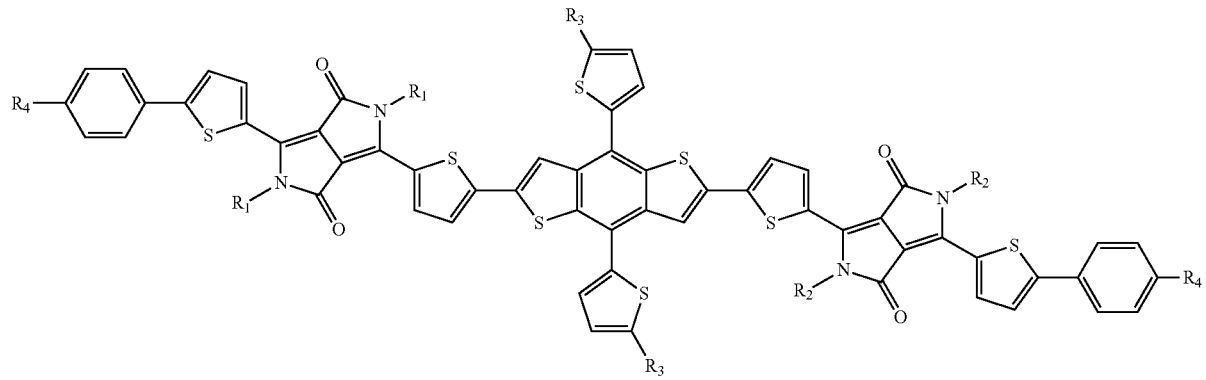

In the General Formula (2), $R_1$ to $R_4$, which are identical to or different from each other, and each represent an alkyl group having 4 to 24 carbon atoms.

The alkyl group having 4 to 24 carbon atoms may be a straight chain or a branched chain, but the branched chain is preferable from the viewpoint of improving solubility. Example thereof include a n-hexyl group, a n-octyl group, a n-dodecyl group, a n-octadecyl group, a 2-ethylhexyl group, a 2-hexyldecyl group, and a 2-decyldodecyl group. Among them, a 2-ethylhexyl group and a 2-hexyldecyl group are preferable.

Organic materials represented by the General Formula (1) and the General Formula (2) are not particularly limited and may be appropriately selected depending on the intended purpose. The organic materials can be synthesized by the method described in Synthesis Example 1 of Examples, which will be described hereinafter.

Specific examples of the organic materials represented by the General Formula (1) and the General Formula (2) include compounds expressed by the following structural formulas. In the compounds expressed by the following structural formulas, Et represents an ethyl group, and Bu represents a butyl group.

<Exemplary Compound 1>

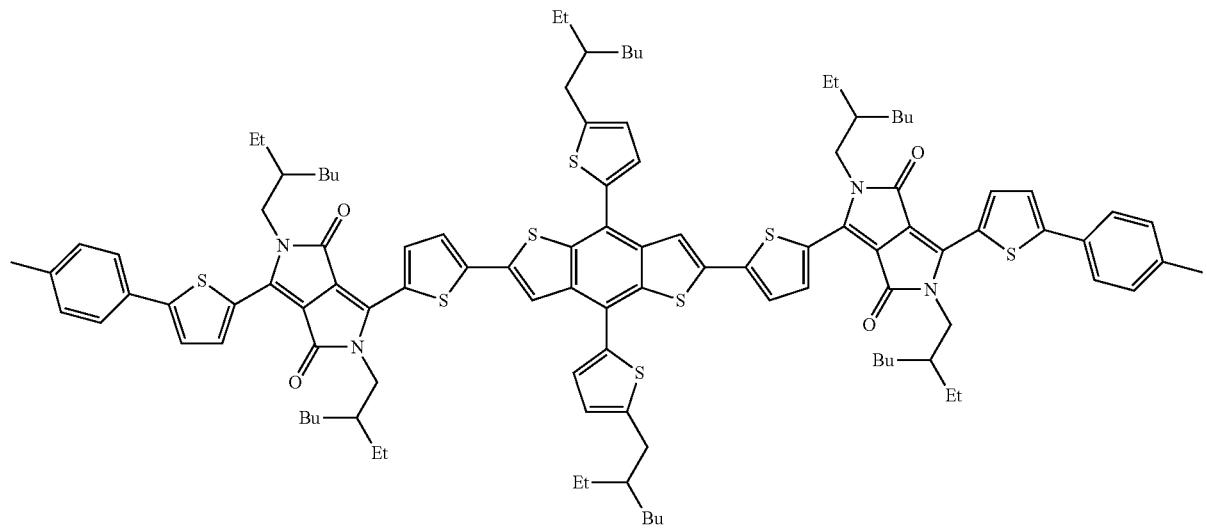

<Exemplary Compound 2>
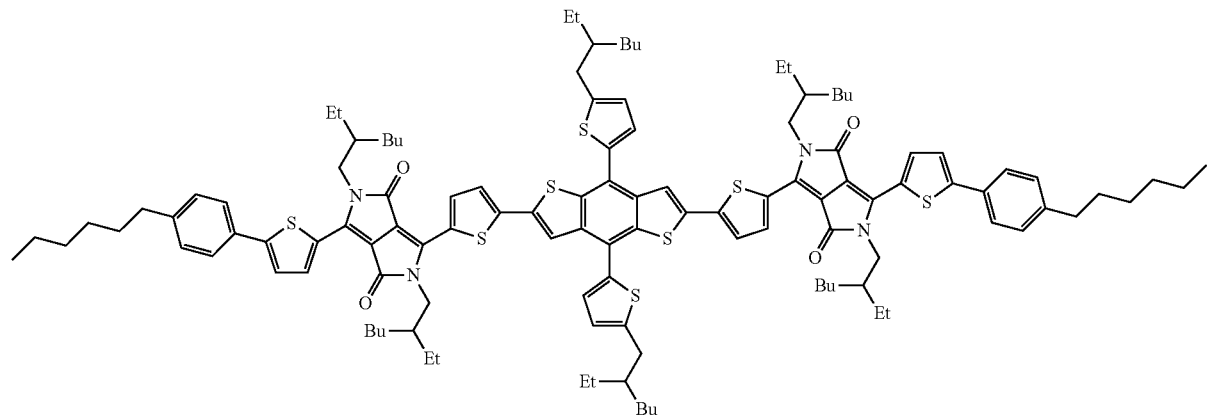
<Exemplary Compound 3>
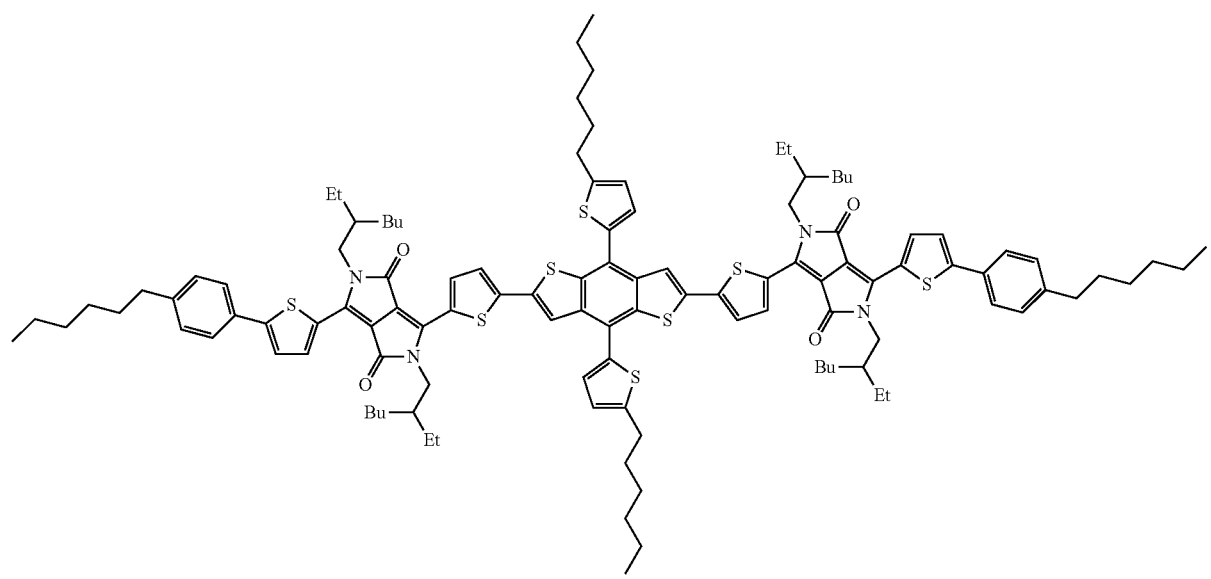
<Exemplary Compound 4>
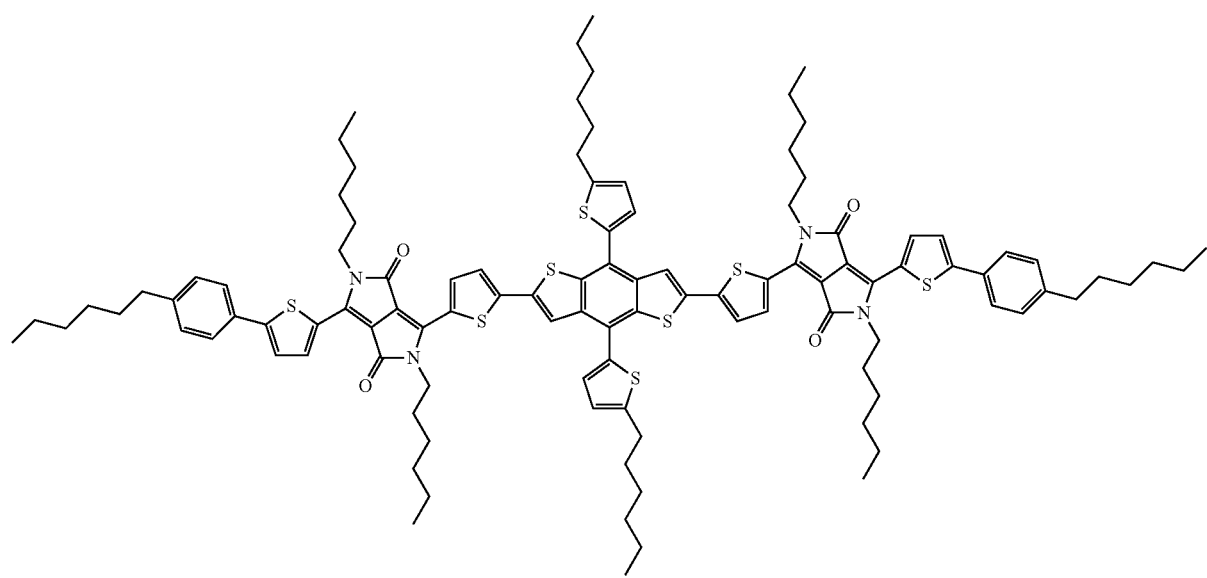

-continued
<Exemplary Compound 5>
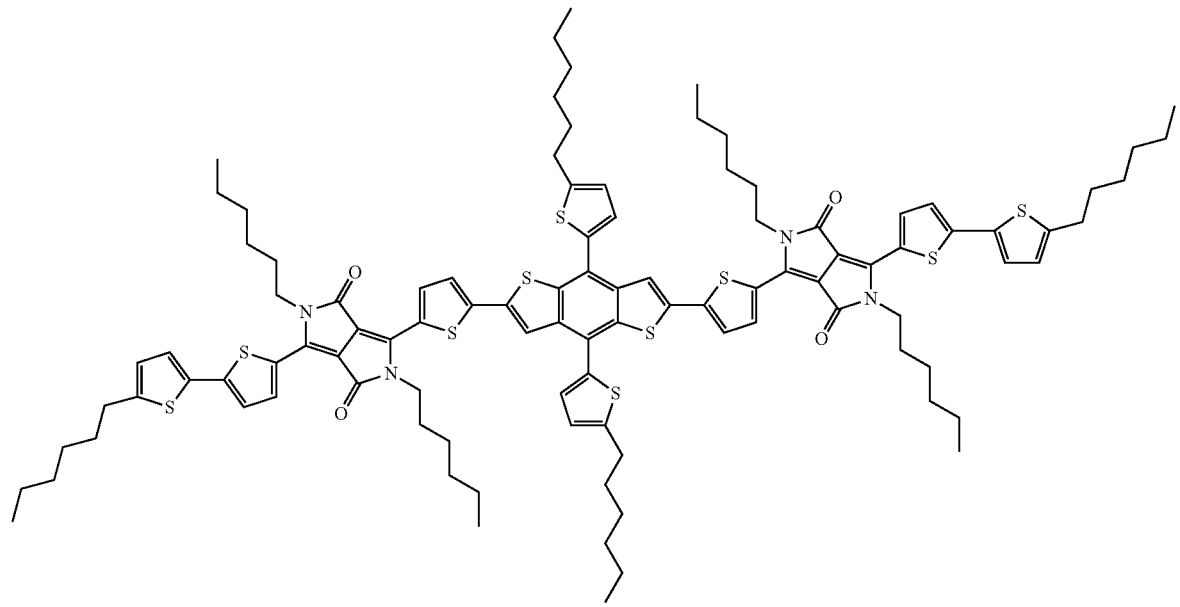
<Exemplary Compound 6>
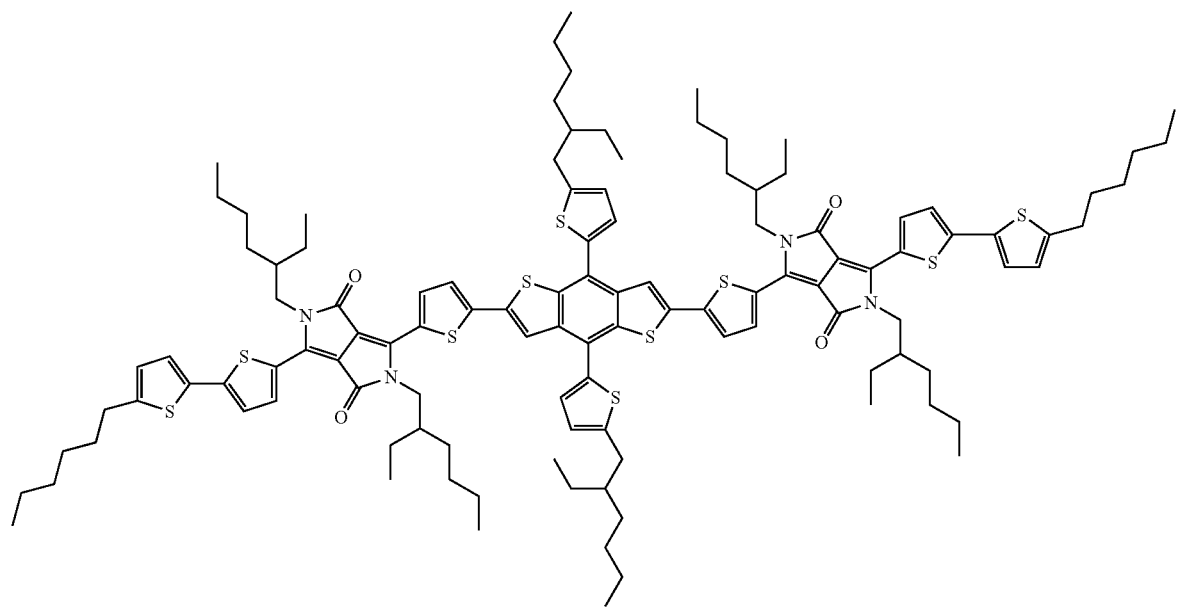

<Exemplary Compound 7>
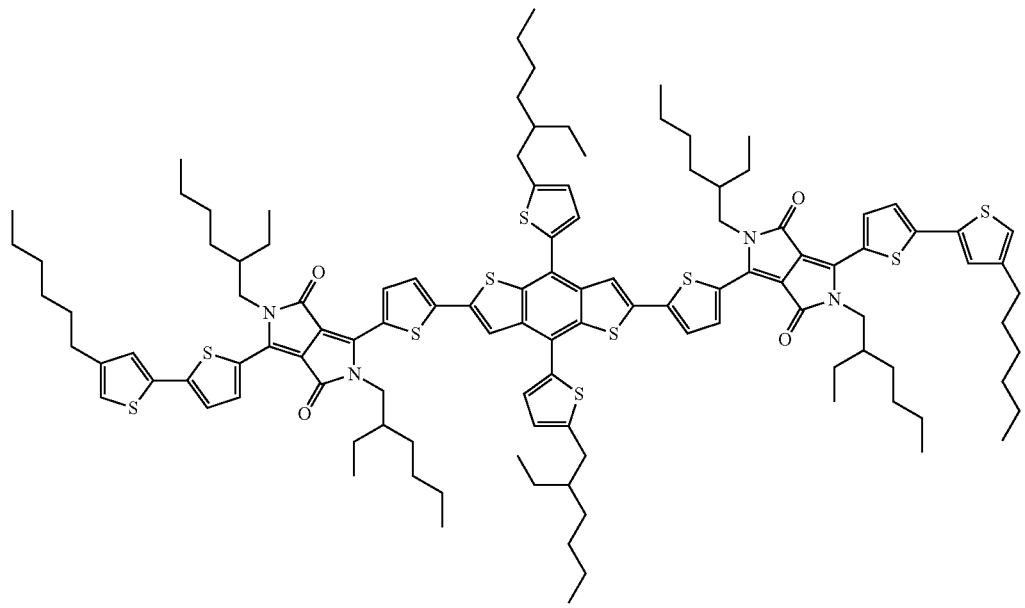
<Exemplary Compound 8>
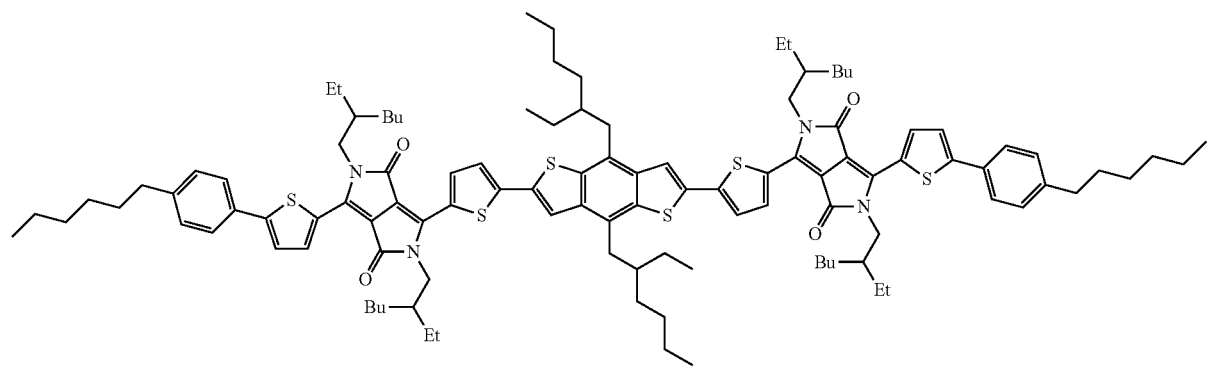
<Exemplary Compound 9>
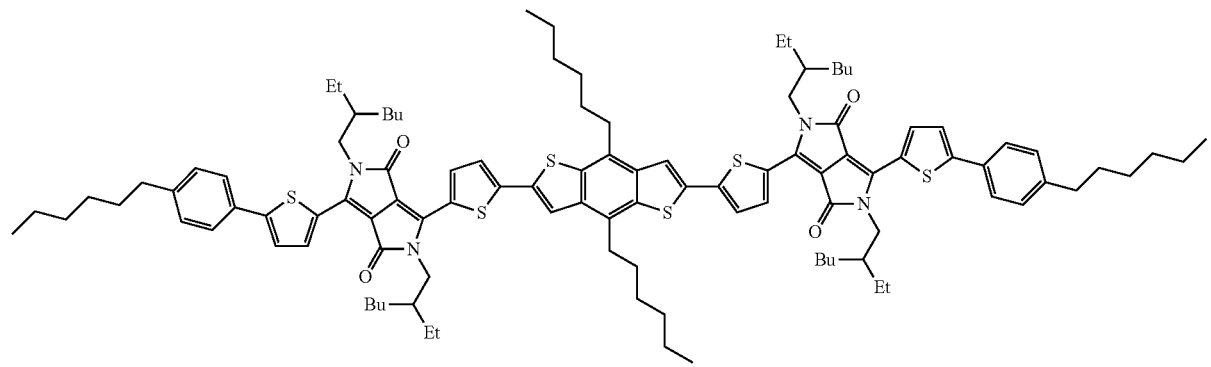

<Exemplary Compound 10>
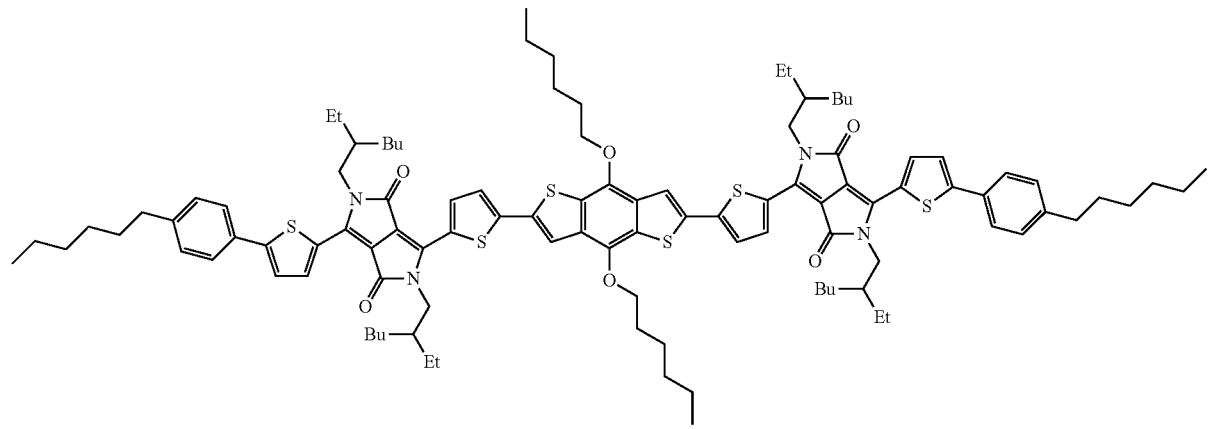
<Exemplary Compound 11>
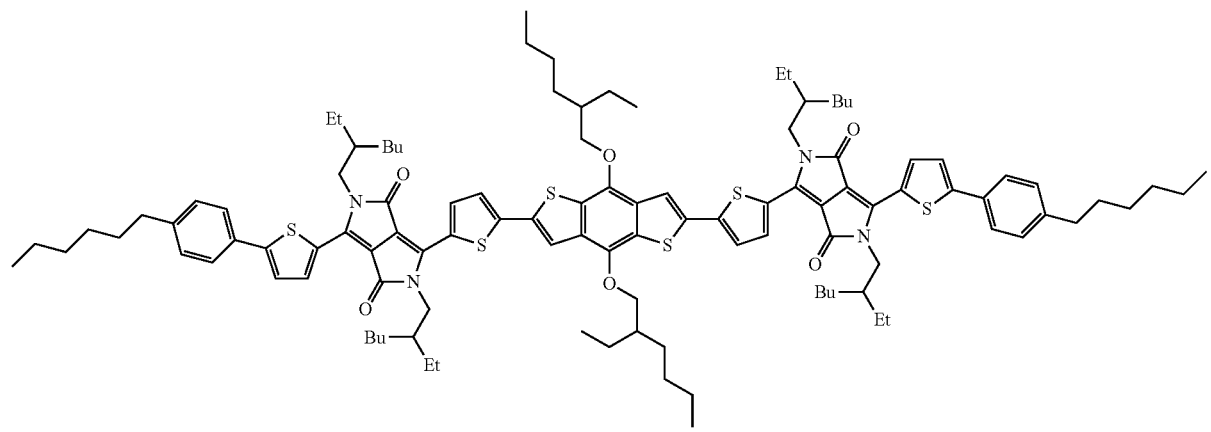
<Exemplary Compound 12>
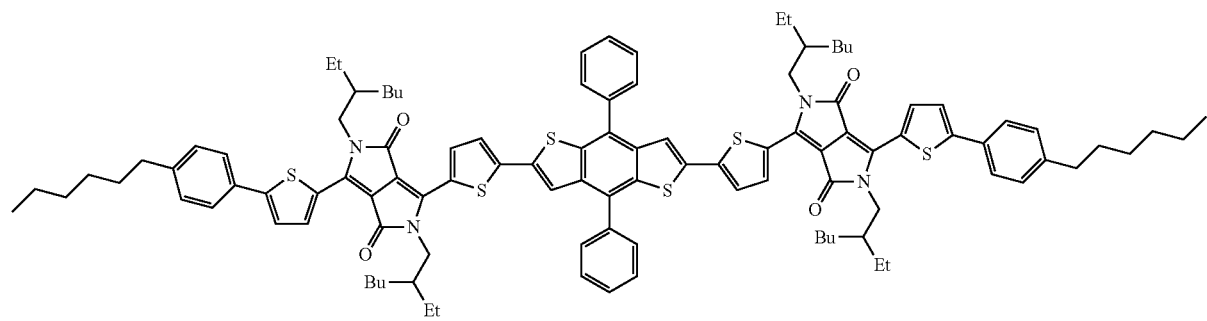

<Exemplary Compound 13>
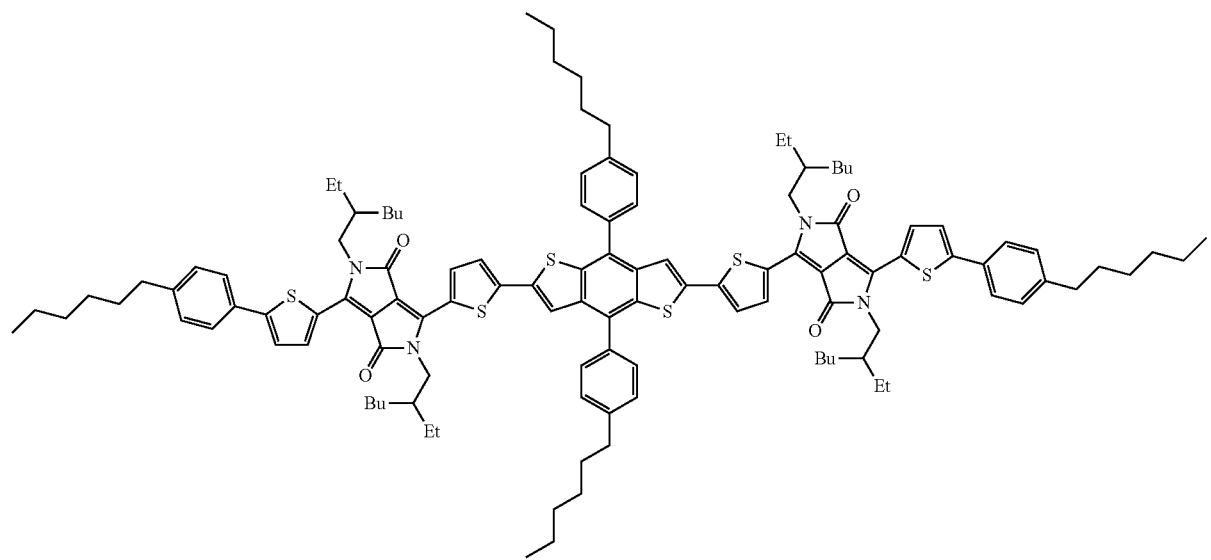
<Exemplary Compound 14>
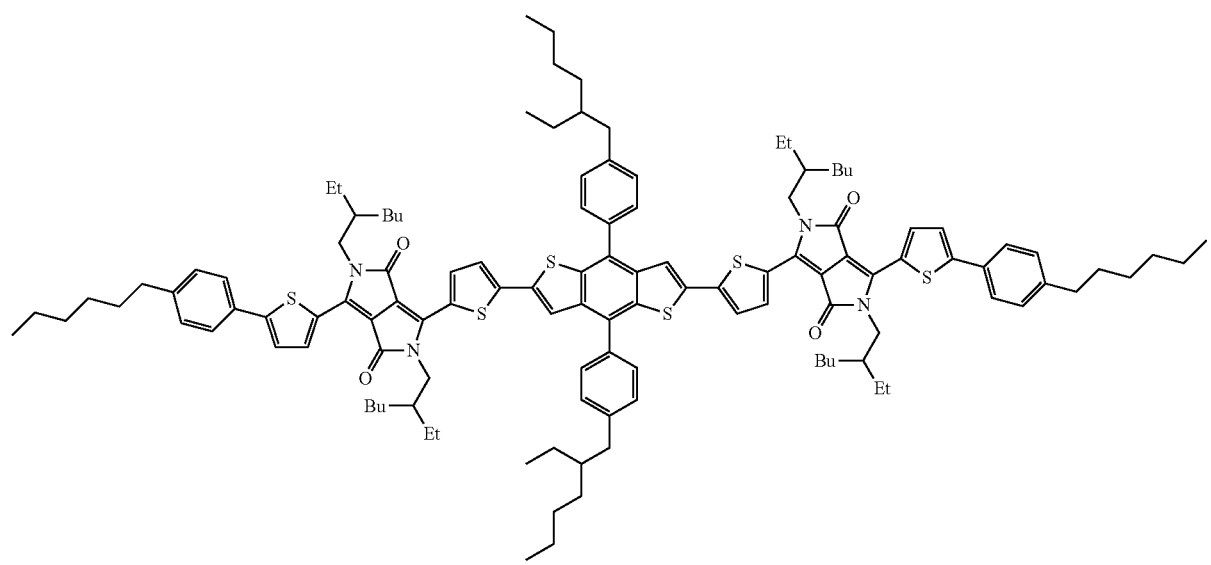

-continued

<Exemplary Compound 15>

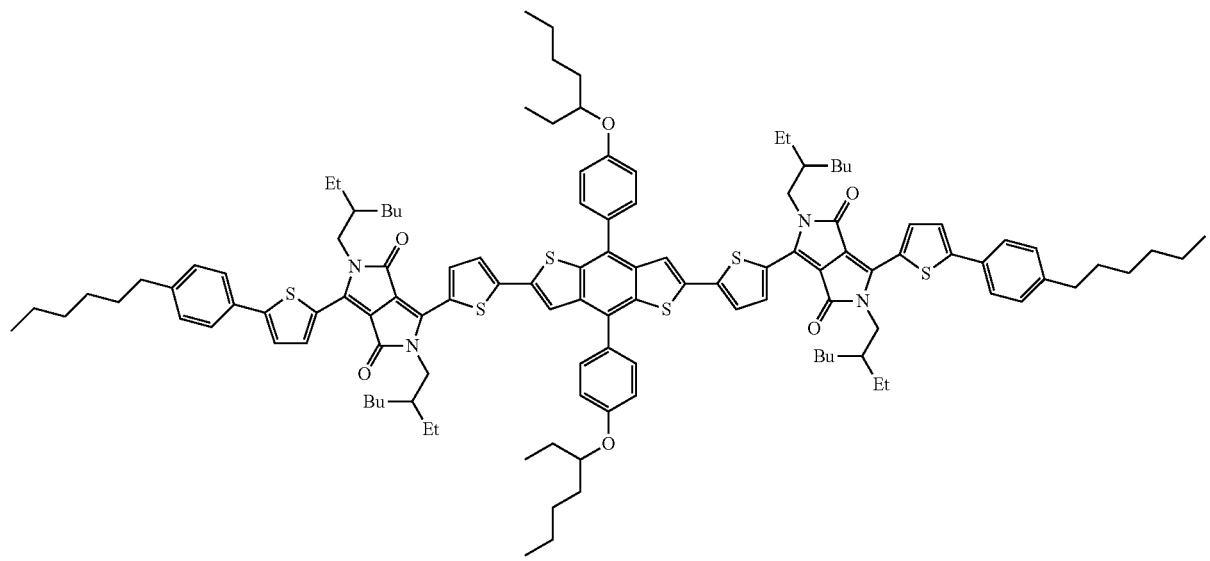

<Exemplary Compound 16>

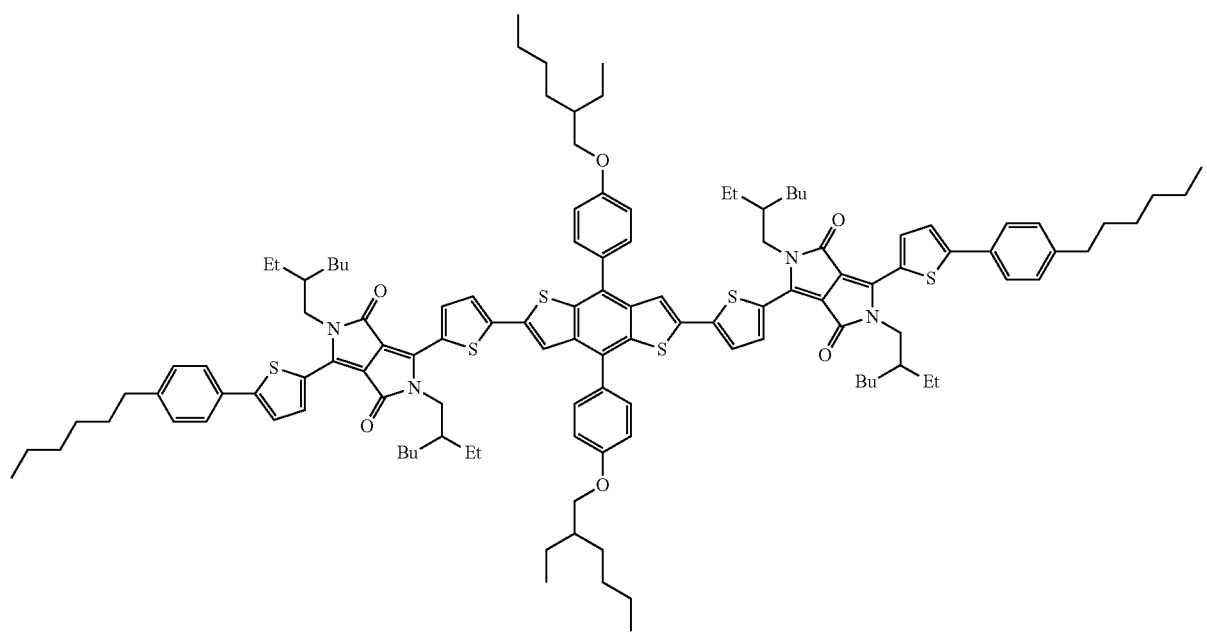

Among them, the Exemplary Compound 2 and the Exemplary Compound 3 are preferable from the viewpoints of solubility and aggregation property.

The organic material represented by General Formula (1) of the present invention can be used for various technical fields because these can absorb a long wavelength and an aggregated structure which is advantageous for charge transportation can be easily obtained. The organic material can be suitably used for the preparation of a photoelectric conversion element having a large open circuit voltage, which will be described hereinafter.

(Solution for Forming Photoelectric Conversion Layer)

A solution for forming a photoelectric conversion layer of the present invention includes the organic material represented by the General Formula (1) of the present invention, a n-type organic material, and an organic solvent, and further includes other components if necessary.

For example, the solution for forming a photoelectric conversion layer is used for forming a photoelectric conversion layer in a photoelectric conversion element, which is described hereinafter.

<Organic Material>

As the organic material, a compound represented by the General Formula (1) can be used.

An amount of the organic material is preferably 0.1% by mass to 4% by mass relative to the total amount of the solution for forming a photoelectric conversion layer.

<n-Type Organic Material>

Examples of the n-type organic material include fullerene and fullerene derivatives. Among them, fullerene derivatives are preferable from the viewpoints of charge separation and charge transportation.

As the fullerene derivatives, appropriately synthesized products or commercially available products may be used.

Examples of the commercially available products include PC71BM (phenyl C71 butyric acid methyl ester, product of Frontier Carbon Corporation), PC61BM (phenyl C61 butyric acid methyl ester, product of Merck), and fullerene indene 2 adduct (product of Aldrich).

An amount of the n-type organic material is preferably 0.1% by mass to 4% by mass relative to the total amount of the solution for forming a photoelectric conversion layer.

<Organic Solvent>

The organic solvent is not particularly limited and may be appropriately selected depending on the intended purpose. Examples thereof include methanol, ethanol, butanol, toluene, xylene, o-chlorophenol, acetone, ethyl acetate, ethylene glycol, tetrahydrofuran, dichloromethane, chloroform, dichloroethane, chlorobenzene, ortho-dichlorobenzene, trichlorobenzene, chloronaphthalene, dimethylformamide, dimethylsulfoxide, N-methylpyrrolidone, and γ-butyrolactone. These may be used alone or in combination of two or more thereof. Among them, chlorobenzene, chloroform, and ortho-dichlorobenzene are preferable.

<Other Components>

The other components are not particularly limited and may be appropriately selected depending on the intended purpose. Examples thereof include various additive agents such as diiodooctane, octanediol, and chloronaphthalene.

(Organic Material Thin Film)

An organic material thin film of the present invention includes the organic material of the present invention and a n-type organic material, and further includes other components if necessary.

The organic material thin film includes a p-type organic material and a n-type organic material. The organic material represented by the General Formula (1) is used as the p-type organic material. Note that, other p-type organic materials may be contained in the organic material thin film.

Examples of the p-type organic material include polymeric materials such as polythiophene compounds, polyphenylene vinylene compounds, polyfluorene compounds, and polyphenylene compounds, and low-molecular-weight materials such as various porphyrins and phthalocyanines.

<n-Type Organic Material>

As the n-type organic material, those similar to the aforementioned n-type organic material in the solution for forming a photoelectric conversion layer can be used.

In the present invention, a p-type semiconductor containing an organic material represented by the General Formula (1) of the present invention, and a n-type semiconductor containing the n-type organic material may be sequentially formed, to thereby form a planar junction interface. However, preferably, these materials are mixed to thereby three-dimensionally form a bulk heterojunction in order to increase the area of the junction interface.

In order to form the bulk heterojunction, when the organic materials having a high solubility are used, the bulk heterojunction can be formed as follows: these aforementioned materials are dissolved in a solvent; the organic material represented by the General Formula (1) of the present invention and the n-type organic material are mixed in a molecular state to thereby prepare a solution; and the solution is coated, and then is dried to remove the solvent. Moreover, an aggregation state of each of the semiconductors can be optimized by heat treatment.

Meanwhile, when the organic materials having a poor solubility are used, a mixed layer can be formed as follows: the n-type organic material is dispersed in a solvent in which the organic material represented by the General Formula (1) of the present invention has been dissolved, to thereby prepare a solution; and the solution is coated. Moreover, an aggregation state of each of the semiconductors can be optimized by heat treatment.

The organic material represented by the General Formula (1) of the present invention can easily form an aggregated structure, is rigid, and thus is excellent in heat resistance. Moreover, it has a deep HOMO level, is excellent in air stability, and is expected to improve the open circuit voltage depending on the material. In addition, a soluble group typified by an alkyl group is introduced to such a rigid molecular skeleton, which ensures solubility to general organic solvents, and an organic material thin film having an orderly aggregation state such as crystallinity, liquid crystallinity, and orientation can be more advantageously formed. Thus, in such a state having a high regularity, high charge transportation can be expected.

In cases where the organic material represented by the General Formula (1) and a n-type organic material are mixed to thereby form an organic material thin film, the organic material represented by the General Formula (1) and the n-type organic material are added to an solvent with a desired mass ratio, and they are dissolved by using a method such as heating, stirring, and ultrasonic irradiation, to thereby prepare a solution, and then the solution is applied on an electrode. In this case, two or more solvents are mixed for use, which can improve photoelectric conversion efficiency of the photoelectric conversion element.

Examples of the methods for forming the organic material thin film include a spin coating method, a blade coating method, a slit die coating method, a screen printing coating method, a bar coater coating method, a mold coating method, a transfer printing method, an immersion pulling-up method, an inkjet method, a spray method, and a vacuum evaporation method. Among them, these can be appropriately selected depending on thickness control, orientation control, and properties of an organic material thin film to be prepared.

For example, when spin coating is performed, a concentration of the organic material represented by the General Formula (1) and a n-type organic material is preferably 5 mg/mL to 30 mg/mL (a mass of the organic material represented by the General Formula (1) and the n-type organic material relative to a volume of a solution containing the organic material containing the structure represented by the General Formula (1), the n-type organic material, and the solvent). A homogeneous organic material thin film can be easily prepared with the aforementioned concentration.

An annealing treatment may be conducted to the prepared organic material thin film under reduced pressure or in an inert atmosphere (nitrogen or argon atmosphere) in order to remove the organic solvent. A temperature of the annealing treatment is preferably 40° C. to 300° C., more preferably 50° C. to 200° C. By conducting the annealing treatment, the laminated layers are fitted together, to thereby increase an effective area, which can increase a short circuit current. Note that, the annealing treatment may be conducted after forming an electrode.

An average thickness of the organic material thin film is preferably 50 nm to 400 nm, more preferably 60 nm to 250 nm. When the average thickness thereof is less than 50 nm, light absorption by the organic material thin film may be lowered, which leads to insufficient carrier generation. When the average thickness thereof is more than 400 nm, transportation efficiency of the carrier generated by light absorption may be further lowered.

The organic material thin film of the present invention can be used for various usages, and is suitably used as a photoelectric conversion layer of a photoelectric conversion element of the present invention, which will be described hereinafter.

(Photoelectric Conversion Element)

A photoelectric conversion element of the present invention includes at least an anode, a cathode, and the organic material thin film of the present invention disposed between the anode and the cathode, and further includes other members if necessary.

<Substrate>

The substrate is not particularly limited and may be appropriately selected depending on the intended purpose so long as it is transparent to visible light. Examples thereof include a glass substrate, a transparent plastic substrate, and a substrate formed of a transparent crystal of an inorganic matter. Among them, the transparent plastic substrate and the glass substrate are preferable from the viewpoints of lightness, robustness, and flexibility.

<Anode, and Cathode>

At least one of the anode and the cathode used is transparent to visible light, and the other may be transparent or opaque.

The electrode that is transparent to visible light is not particularly limited, and known products such as a normal photoelectric conversion element or a liquid crystal panel may be used for the electrode. Examples thereof include electroconductive metallic oxides such as tin-doped indium oxide (referred to as ITO hereinafter), fluorine-doped tin oxide (referred to as FTO hereinafter), antimony-doped tin oxide (referred to as ATO hereinafter), aluminium-doped zinc oxide (referred to as AZO hereinafter), and gallium-doped zinc oxide (referred to as GZO hereinafter).

An average thickness of the electrode that is transparent to visible light is preferably 5 nm to 10 μm, more preferably 50 nm to 1 μm.

The electrode that is transparent to visible light is preferably disposed on a substrate containing a product transparent to visible light in order to maintain a certain hardness, and a product of the electrode and the substrate that are integrated can also be used. Examples thereof include FTO coated glass, ITO coated glass, zinc oxide:aluminium coated glass, an FTO coated transparent plastic film, and an ITO coated transparent plastic film.

The electrode transparent to visible light may be an electrode containing a substrate (e.g., a glass substrate) on which a metal electrode is disposed so as to have a structure through which light can pass (e.g., a mesh-patterned structure or a stripe-pattered structure); or may be an electrode where carbon nanotube, graphene or the like is laminated on the substrate so as to have transparency. These may be used alone or in combination of two or more thereof, or may be laminated.

Also, in order to reduce substrate resistance, a metal lead wire may be used. Examples of the material of the metal lead wire include metals such as aluminium, copper, silver, gold, platinum, and nickel. A method for producing the metal lead wires is, for example, a method where a metal membrane is disposed on a substrate by, for example a vapor deposition method, a sputtering method, or a pressure joint method, followed by forming ITO or FTO thereon.

In cases where an opaque electrode is used for the anode or the cathode, examples of the material of the opaque electrode include metals such as platinum, gold, silver, copper, and Al; and graphite. These may be used alone or in combination of two or more thereof.

An average thickness of the opaque electrode is not particularly limited and may be appropriately selected depending on the intended purpose.

Here, in a so-called normal-type photoelectric conversion element (see FIG. 1), a cathode is preferably an Al electrode. Meanwhile, in a so-called inverse-type photoelectric conversion element (see FIG. 2), a cathode is preferably an Ag electrode.

<Hole Transport Layer>

In the normal-type photoelectric conversion element (see FIG. 1), a hole transport layer is laminated on an anode. Meanwhile, in the inverse-type photoelectric conversion element (see FIG. 2), a hole transport layer is laminated on a photoelectric conversion layer. That is, collection efficiency of the hole can be improved by disposing a hole transport layer on the surface of the anode or the surface of the photoelectric conversion layer.

The hole transport layer is not particularly limited and may be appropriately selected depending on the intended purpose. It can be formed, for example, by a method for coating an electroconductive polymer such as PEDOT:PSS (polyethylenedioxythiophene:polystyrene sulfonic acid); and a sol-gel method and a sputtering method using inorganic compounds having hole transporting property such as molybdenum oxide, vanadium oxide, and nickel oxide.

In the normal-type photoelectric conversion element, a hole transport layer preferably contains an electroconductive polymer, and in the inverse-type photoelectric conversion element, it preferably contains molybdenum oxide.

An average thickness of the hole transport layer is not particularly limited and may be appropriately selected depending on the intended purpose. The hole transport layer preferably covers the whole surface as thinly as possible, and the average thickness thereof is more preferably 1 nm to 50 nm.

<Electron Transport Layer>

In the normal-type photoelectric conversion element, the electron transport layer is laminated on the photoelectric conversion layer. Meanwhile, in the inverse-type photoelectric conversion element, the electron transport layer is laminated on the cathode.

Materials of the electron transport layer are not particularly limited and may be appropriately selected depending on the intended purpose. Examples thereof include electron-accepting organic materials (e.g., perylenetetracarboxylic anhydride, perylenetetracarboxylic diimide, oxazole derivatives, triazol derivatives, phenanthroline derivatives, phosphine oxide derivatives, fullerene compounds, carbon nanotube (CNT), and CN-PPV), zinc oxide, titanium oxide, lithium fluoride, and calcium metals. These may be used alone or in combination of two or more thereof. Among them, in the normal-type photoelectric conversion element, lithium fluoride is preferable, and in the inverse-type photoelectric conversion element, zinc oxide is preferable.

The electron transport layer can be formed by, for example, a sol-gel method, a vapor deposition method, or a sputtering method.

An average thickness of the electron transport layer is not particularly limited and may be appropriately selected depending on the intended purpose.

The electron transport layer preferably covers the whole surface as thinly as possible, and the average thickness thereof is more preferably 1 nm to 50 nm.

<Photoelectric Conversion Layer>

The photoelectric conversion layer includes the organic material thin film containing the organic material represented by the General Formula (1) of the present invention.

An average thickness of the photoelectric conversion layer is preferably 50 nm to 400 nm, more preferably 60 nm to 250 nm. When the average thickness thereof is less than 50 nm, light absorption by the photoelectric conversion layer may be lowered, and generation of the carrier may be insufficient. When it is more than 400 nm, transportation efficiency of the carrier generated by light absorption may be further lowered.

<Other Members>

The aforementioned other members are not particularly limited and may be appropriately selected depending on the intended purpose. Examples thereof include a gas barrier layer, a protective layer, and a buffer layer.

Examples of materials of the gas barrier layer include inorganic materials such as silicone nitride and silicone oxide.

In a photoelectric conversion element of the present invention, two or more photoelectric conversion elements may be laminated (in a tandem manner) through one or more intermediate electrode(s), to thereby form a serial junction. The laminated constitution is, for example, substrate/anode/hole transport layer/first photoelectric conversion layer/intermediate electrode/second photoelectric conversion layer/electron transport layer/cathode. Laminating them in this manner can improve an open circuit voltage.

In the aforementioned laminated constitution, at least one layer of the photoelectric conversion layers includes an organic material thin film containing the organic material represented by the General Formula (1), and the other layer preferably contains another organic material having a different absorption wavelength with the organic material represented by the General Formula (1), in order not to lower a short circuit current.

Examples of the another organic material include polymeric materials such as polythiophene compounds, polyphenylene vinylene compounds, polyfluorene compounds, and polyphenylene compounds; and low-molecular-weight materials such as various porphyrins and phthalocyanines.

Here, the photoelectric conversion element of the present invention will be described with reference to the figures.

FIG. 1 is a so-called normal-type photoelectric conversion element 10, configured to sequentially dispose an anode 2, a hole transport layer 3, a photoelectric conversion layer 4, an electron transport layer 5, and a cathode 6 on a substrate 1. The photoelectric conversion layer 4 includes an organic material thin film containing the organic material represented by the General Formula (1).

FIG. 2 is a so-called inverse-type photoelectric conversion element 20, configured to sequentially dispose a cathode 6, an electron transport layer 5, a photoelectric conversion layer 4, a hole transport layer 3, and an anode 2 on a substrate 1. The photoelectric conversion layer 4 includes an organic material thin film containing the organic material represented by the General Formula (1).

The photoelectric conversion element of the present invention has high open circuit voltage, can absorb light of a wide wavelength range, and is excellent in charge transport ability, and thus can be suitably used for an organic thin film solar cell, for example.

EXAMPLES

The present invention will be described with reference to the following examples. However, it should be noted that the present invention is not limited to these Examples.

Synthesis Example 1

In accordance with the following scheme, 2DPP-TBDT, which is the Exemplary Compound 2, was synthesized. Note that, compound 7 described in the scheme was synthesized based on Angewandte Chemie, International Edition (2011), 50, (41), 9697-9702.

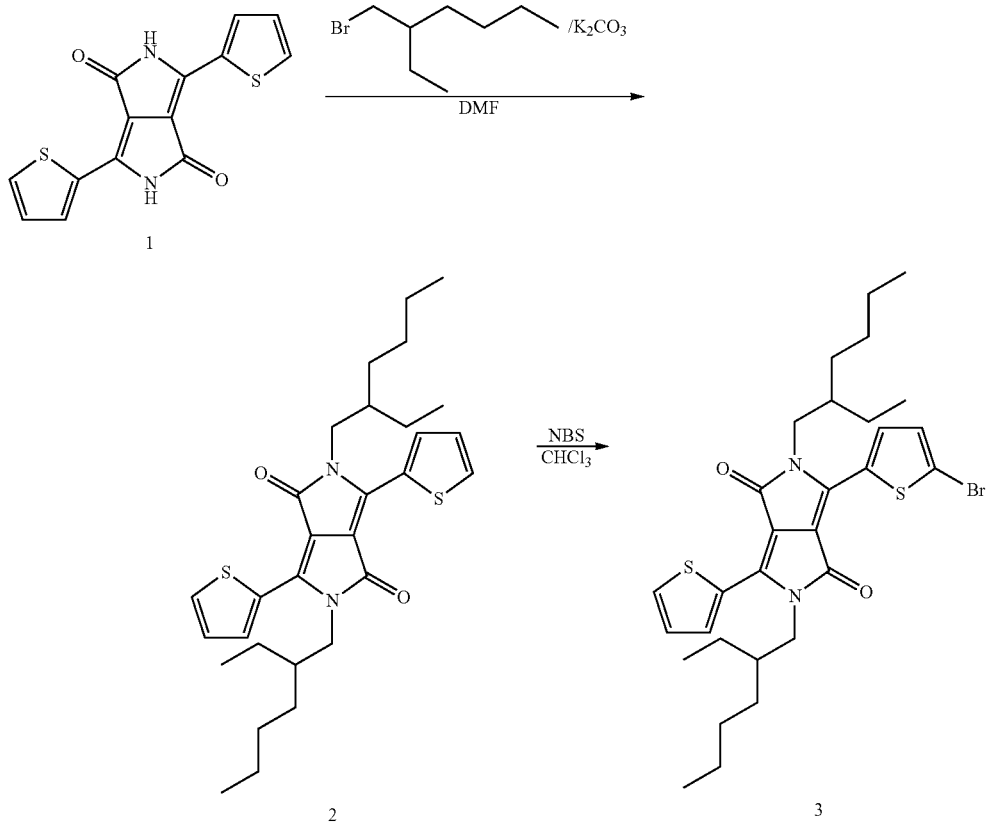

-continued
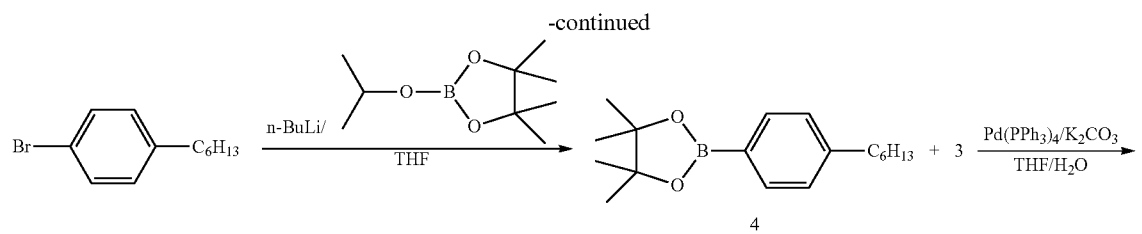
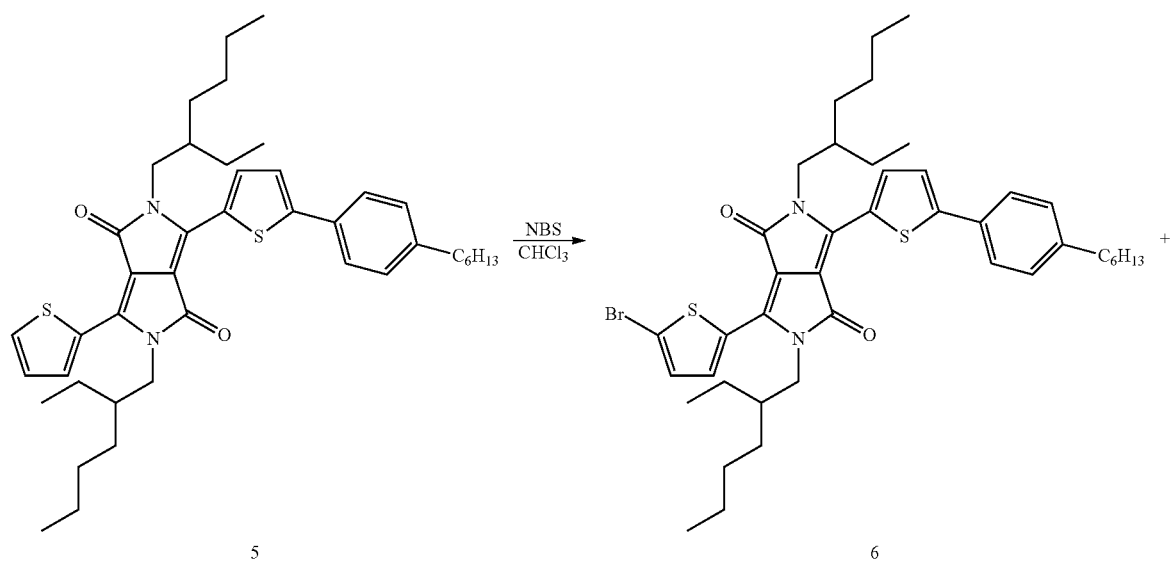
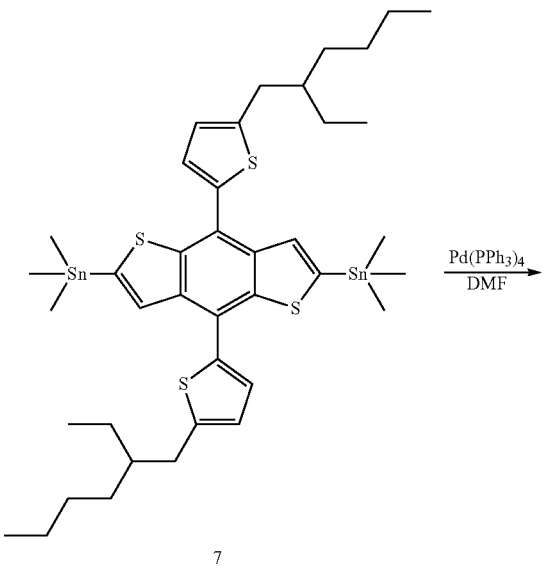

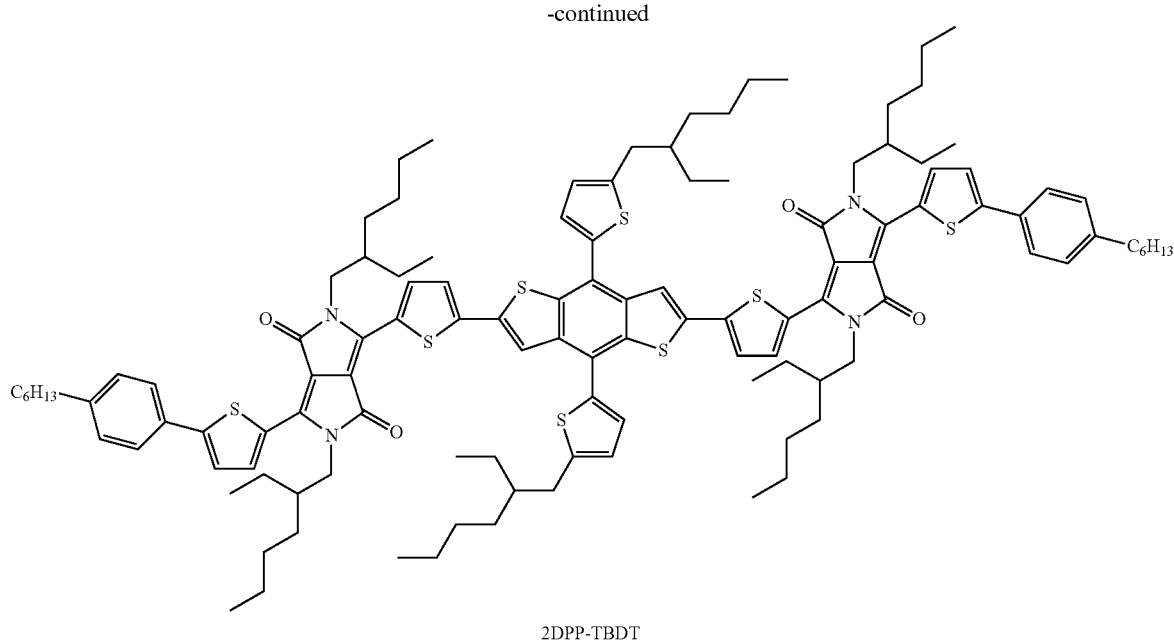

2DPP-TBDT

<Synthesis of Compound 2>

Compound 1 (10.0 g, 33.3 mmol), 2-ethylhexyl bromide (19.3 g, 99.9 mmol), and K$_2$CO$_3$ (18.4 g, 133 mmol) were mixed in a dry DMF (300 mL), and were stirred at 120° C. for 24 hours. After cooling to room temperature, the reaction mixture was poured into a large amount of ice water in order to form precipitates. The obtained precipitates were collected through a filtration, and were washed with water and methanol.

The obtained product was purified by silica gel column chromatography (eluent: CHCl$_3$/hexane=1:1, v/v), was recrystallized with CHCl$_3$/methanol, and was dried under vacuum, to thereby obtain compound 2 as a reddish brown solid (8.89 g, yield=51%).

The results of $^1$H NMR and $^{13}$C NMR for the obtained compound 2 are shown below.

Note that, analysis of $^1$H NMR and $^{13}$C NMR were carried out by AVANCE III 500 (product of Bruker). These analyses were conducted in the same manner hereinafter.

$^1$H NMR (500 MHz, CDCl$_3$):

δ8.89 (dd, J=4.0 Hz, 1.5 Hz, 2H), 7.63 (dd, J=5.0 Hz, 1.5 Hz, 2H), 7.27 (dd, J=5.0 Hz, 4.0 Hz, 2H), 4.07-3.98 (m, 4H), 1.89-1.84 (m, 2H), 1.40-1.20 (m, 16H), 0.89-0.84 (m, 12H).

$^{13}$C NMR (125 MHz, CDCl$_3$):

δ161.78, 140.45, 135.25, 130.49, 129.87, 128.42, 107.98, 45.89, 39.11, 30.24, 28.39, 23.5 8, 23.06, 14.01, 10.50.

<Synthesis of Compound 3>

Compound 2 (5.00 g, 9.52 mmol) was stirred in a dry CHCl$_3$ (300 mL), to thereby prepare a solution of compound 2. Then, N-bromosuccinimide (NBS, 1.69 g, 9.52 mmol) was slowly added thereto at 0° C. The obtained mixture was heated to room temperature, and was stirred overnight. Water was poured to the obtained reaction mixture, which was then extracted with CHCl$_3$. The obtained organic phase was washed with water, and was dried with MgSO$_4$ anhydrate. After the resultant mixture had been subjected to filtration and evaporation, the product was purified by silica gel column chromatography (eluent: toluene/hexane=4:1, v/v), was recrystallized with CHCl$_3$/methanol, and was dried under vacuum, to thereby obtain compound 3 as a reddish brown solid (2.59 g, yield=45%).

For the obtained compound 3, the results of $^1$H NMR and $^{13}$C NMR were shown below.

$^1$H NMR (500 MHz, CDCl$_3$):

δ8.90 (dd, J=4.0 Hz, 1.5 Hz, 1H), 8.63 (d, J=4.0 Hz, 1H), 7.64 (dd, J=5.0 Hz, 1.0 Hz, 1H), 7.28-7.26 (m, 2H), 7.22 (d, J=4.5 Hz, 1H), 4.03-3.99 (m, 2H), 3.98-3.92 (m, 2H), 1.88-1.80 (m, 2H), 1.38-1.23 (m, 16H), 0.90-0.84 (m, 12H).

$^{13}$C NMR (125 MHz, CDCl$_3$):

δ161.69, 161.52, 140.92, 138.98, 135.53, 135.09, 131.40, 131.29, 130.82, 129.78, 128.51, 118.62, 108.20, 107.84, 45.98, 45.95, 39.15, 39.09, 30.22, 28.36, 23.60, 23.57, 23.05, 23.04, 14.01, 10.49.

<Synthesis of Compound 4>

In a dry THF (200 mL), 1-bromo-4-hexylbenzene (5.00 g, 20.7 mmol) was stirred to thereby obtain a solution. Then, n-butyllithium (1.62 M, 15.4 mL, 24.9 mmol in hexane) was added dropwise thereto at −78° C. The obtained mixture was allowed to react at −78° C. for 1 hour. Next, 2-isopropoxy-4,4,5,5-tetramethyl-1,3,2-dioxaborolane (4.63 g, 24.9 mmol) was added to the resultant mixture, and the obtained mixture was stirred at room temperature overnight. The obtained reaction mixture was poured to water, and the mixture was then extracted with diethyl ether. The obtained organic phase was washed with water, and was dried with MgSO$_4$ anhydrate. After the resultant mixture had been subjected to filtration and evaporation, the product was purified by silica gel column chromatography (eluent: hexane), and was dried under vacuum, to thereby obtain compound 4 as a colorless oil (4.09 g, yield=68%).

For the obtained compound 4, the results of $^1$H NMR and $^{13}$C NMR were shown below.

$^1$H NMR (500 MHz, CDCl$_3$):

δ7.73 (d, J=8.0 Hz, 2H), 7.18 (d, J=8.0 Hz, 2H), 2.60 (t, J=8.0 Hz, 2H), 1.63-1.57 (m, 2H), 1.33 (s, 12H), 1.30-1.27 (m, 6H), 0.87 (t, J=7.0 Hz, 3H).

$^{13}$C NMR (125 MHz, CDCl$_3$):

δ146.39, 134.91, 127.93, 83.58, 36.26, 31.79, 31.37, 29.03, 24.91, 22.66, 14.14.

<Synthesis of Compound 5>

Compound 3 (2.50 g, 4.14 mmol) and the compound 4 (1.70 g, 4.55 mmol) were mixed in a dry THF (40 mL), to thereby obtain a mixture. Then, $Pd(PPh_3)_4$ (0.24 g, 0.21 mmol) and an aqueous $K_2CO_3$ solution (2.0 M, 20 mL; bubbled with nitrogen before use) were added to the mixture. The obtained mixture was stirred at 60° C. for 24 hours. The resultant mixture was cooled to room temperature, and then the reaction mixture was poured to water, and the mixture was then extracted with $CHCl_3$. The obtained organic phase was washed with water, and was dried with $MgSO_4$ anhydrate. After the resultant mixture had been subjected to filtration and evaporation, the product was purified by silica gel column chromatography (eluent: $CHCl_3$), was recrystallized with $CHCl_3$/methanol, and was dried under vacuum, to thereby obtain compound 5 as a dark purple solid (2.75 g, yield=96%).

The results of $^1H$ NMR and $^{13}C$ NMR for the obtained compound 5 are shown below.

$^1H$ NMR (500 MHz, $CDCl_3$):

δ8.98 (d, J=4.0 Hz, 1H), 8.87 (dd, J=4.0 Hz, 1.0 Hz, 1H), 7.61 (dd, J=5.0 Hz, 1.0 Hz, 1H), 7.59 (d, J=8.5 Hz, 2H), 7.43 (d, J=4.0 Hz, 1H), 7.28-7.26 (m, 1H), 7.24 (d, J=8.0 Hz, 2H), 4.10-4.00 (m, 4H), 2.64 (t, J=7.5 Hz, 2H), 1.97-1.92 (m, 1H), 1.90-1.85 (m, 1H), 1.67-1.60 (m, 2H), 1.42-1.23 (m, 22H), 0.92-0.84 (m, 15H).

$^{13}C$ NMR (125 MHz, $CDCl_3$):

δ161.91, 161.68, 150.31, 144.22, 140.63, 139.74, 137.10, 135.00, 130.62, 130.28, 129.97, 129.23, 128.40, 128.23, 126.10, 124.04, 108.21, 107.83, 45.98, 45.93, 39.24, 39.12, 35.76, 31.71, 31.29, 30.28, 30.26, 28.95, 28.59, 28.40, 23.71, 23.60, 23.12, 23.07, 22.61, 14.09, 14.06, 14.02, 10.58, 10.53.

<Synthesis of Compound 6>

Compound 5 (2.50 g, 3.65 mmol) was stirred in a thy $CHCl_3$ (50 mL) to thereby obtain a solution, and then N-bromosuccinimide (NBS, 0.71 g, 4.01 mmol) was slowly added thereto at 0° C. The obtained mixture was heated to room temperature, and then was stirred over night. The obtained reaction mixture was poured to water, and the mixture was then extracted with $CHCl_3$. The obtained organic phase was washed with water, and then was dried with $MgSO_4$ anhydrate. After the resultant mixture had been subjected to filtration and evaporation, the product was purified by silica gel column chromatography (eluent: $CHCl_3$), was recrystallized with $CHCl_3$/methanol, and was dried under vacuum, to thereby obtain compound 6 as a dark brown solid (2.70 g, yield=97%).

For the obtained compound 6, the results of $^1H$ NMR and $^{13}C$ NMR are shown below.

$^1H$ NMR (500 MHz, $CDCl_3$): δ

8.99 (d, J=4.0 Hz, 1H), 8.61 (d, J=4.0 Hz, 1H), 7.58 (d, J=8.5 Hz, 2H), 7.43 (d, J=4.5 Hz, 1H), 7.24 (d, J=8.5 Hz, 2H), 7.21 (d, J=4.0 Hz, 1H), 4.10-4.01 (m, 2H), 4.00-3.90 (m, 2H), 2.64 (t, J=8.0 Hz, 2H), 1.96-1.90 (m, 1H), 1.87-1.82 (m, 1H), 1.66-1.60 (m, 2H), 1.41-1.23 (m, 22H), 0.92-0.89 (m, 15H).

$^{13}C$ NMR (125 MHz, $CDCl_3$):

δ161.80, 161.39, 150.65, 144.31, 141.04, 138.19, 137.41, 134.81, 131.42, 131.36, 130.55, 129.24, 128.13, 126.10, 124.09, 118.28, 108.43, 107.67, 46.02, 39.23, 39.15, 35.77, 31.71, 31.28, 30.36, 30.24, 28.95, 28.57, 28.37, 23.70, 23.62, 23.11, 23.05, 22.97, 22.61, 14.08, 14.06, 14.02, 10.57, 10.52.

<Synthesis of 2DPP-TBDT>

The compound 6 (0.80 g, 0.88 mmol) and the compound 7 (1.42 g, 1.86 mmol) were mixed in a dry DMF (20 mL), to thereby obtain a mixture solution. Then, $Pd(PPh_3)_4$ (0.05 g, 0.04 mmol) was added thereto. The obtained mixture was stirred at 85° C. for 24 hours. The obtained mixture was cooled to room temperature, the obtained reaction mixture was poured to water, and the mixture was then extracted with $CHCl_3$. The obtained organic phase was washed with water, and then was dried with $MgSO_4$ anhydrate. After the resultant mixture had been subjected to filtration and evaporation, the product was purified by silica gel column chromatography (eluent: $CHCl_3$), was recrystallized with $CHCl_3$/methanol, and was dried under vacuum, to thereby obtain 2DPP-TBDT as a dark purple solid. The obtained compound was further purified by gel permeation chromatography (GPC) before use (1.39 g, yield-=81%).

For the obtained 2DPP-TBDT, the results of $^1H$ NMR and $^{13}C$ NMR are shown below.

$^1H$ NMR (500 MHz, $CDCl_3$):

δ9.02 (d, J=4.0 Hz, 2H), 9.00 (d, J=4.0 Hz, 2H), 7.62 (s, 2H), 7.48 (d, J=7.5 Hz, 4H), 7.39 (d, J=3.5 Hz, 2H), 7.34 (d, J=4.0 Hz, 2H), 7.25 (d, J=4.0 Hz, 2H) 7.12 (d, J=7.5 Hz, 4H), 6.99 (d, J=3.5 Hz, 2H), 4.00-3.94 (m, 8H), 2.96 (d, J=6.5 Hz, 4H), 2.54-2.50 (m, 4H), 1.91-1.85 (m, 4H), 1.82-1.77 (m, 2H), 1.57-1.28 (m, 64H), 1.03 (t, J=7.5 Hz, 6H), 0.97 (t, J=6.8 Hz, 6H), 0.95-0.87 (m, 30H).

$^{13}C$ NMR (125 MHz, $CDCl_3$):

δ161.41, 161.36, 149.97, 146.26, 144.03, 141.79, 139.77, 138.96, 138.52, 137.36, 136.75, 136.65, 136.52, 130.42, 129.07, 128.99, 128.18, 128.08, 125.74, 125.54, 123.74, 120.56, 120.29, 108.41, 107.89, 45.88, 41.43, 39.45, 39.34, 35.72, 34.50, 32.67, 31.69, 31.15, 30.40, 29.03, 29.01, 28.61, 25.78, 23.66, 23.20, 23.16, 23.13, 22.62, 14.24, 14.14, 14.09, 10.93, 10.68, 10.58.

The elemental analysis values of the obtained 2DPP-TBDT ($C_{118}H_{150}N_4O_4S_8$) were shown below.

TABLE A

|  | C | H | N | O | S |
|---|---|---|---|---|---|
| Found (%) | 72.75 | 7.70 | 2.80 | — | — |
| Calcd. (%) | 72.87 | 7.77 | 2.88 | 3.29 | 13.19 |

Comparative Example 1

Preparation of Photoelectric Conversion Element

A glass substrate with a patterned ITO was subjected to ultrasonic washing and UV ozone cleaning. A solution of PEDOT:PSS (polyethylene dioxythiophene:polystyrene sulfonic acid, product of H. C. Stark, Clevios P VP AI4083) was coated on the glass substrate by a spin coating method (speed of rotation: 3,000 rpm), and then the resultant product was dried at 130° C. for 10 minutes.

Next, P3HT (poly-3-hexylthiophene) and PC61BM (phenyl C61 butyric acid methyl ester, product of Merck) were dissolved in chlorobenzene (1 mL) at a ratio of 17 mg:17 mg. Then, the resultant mixture was stirred overnight or longer in a glove box that had been purged with nitrogen, to thereby prepare a solution for forming a photoelectric conversion layer.

Then, the obtained solution for forming a photoelectric conversion layer was coated for film formation on the PEDOT:PSS film by a spin coating method in the atmosphere, to thereby form a film thereon. Then, the film was dried at 140° C. for 10 minutes, to thereby form a photoelectric conversion layer. The obtained photoelectric conversion layer was found to have an average thickness of 100 nm.

Next, using a vacuum evaporation method under $1 \times 10^{-6}$ Torr, a lithium fluoride film was formed on the photoelectric conversion layer so that the thickness thereof was 1 nm, and an Al electrode film was formed thereon so that the thickness thereof was 80 nm, to thereby form a photoelectric conversion element.

<Evaluation>

Solar cell performances of the obtained photoelectric conversion element were measured by SRO-25GD (product of Bunkoukeiki Co., Ltd.) upon irradiation of simulated solar light (AM1.5, 100 mW/cm$^2$). The obtained photoelectric conversion element was found to have an open end voltage of 560 mV, a short-circuit current density of 6.96 mA/cm$^2$, a fill factor of 0.60, and a photoelectric conversion efficiency of 2.33%.

Example 1

A solution of PEDOT:PSS was coated on a glass substrate with a patterned ITO that had been subjected to ultrasonic washing and UV ozone cleaning in the same manner as in Comparative Example 1.

Next, an organic material shown in the Exemplary Compound 2 and PC71BM (phenyl C71 butyric acid methyl ester, product of Frontier Carbon Corporation) were dissolved in chloroform (1 mL) at a ratio of 7 mg:7 mg. The resultant mixture was stirred overnight or longer in a glove box that had been purged with nitrogen, to thereby prepare a solution for forming a photoelectric conversion layer.

Then, the obtained solution for forming a photoelectric conversion layer was coated on the PEDOT:PSS film in the atmosphere by a spin coating method, to thereby form a film thereon. Then, the film was dried at 120° C. for 10 minutes, to thereby form a photoelectric conversion layer. The obtained photoelectric conversion layer was found to have an average thickness of 110 nm.

Next, using a vacuum evaporation method under 1×10$^{-6}$ Torr, a lithium fluoride film was formed on the photoelectric conversion layer so that the thickness thereof was 1 nm, and an Al electrode film was formed thereon so that the thickness thereof was 80 nm, to thereby form a photoelectric conversion element.

<Evaluation>

Solar cell performances of the prepared photoelectric conversion element were measured upon irradiation of simulated solar light (AM1.5, 100 mW/cm$^2$) in the same manner as in Comparative Example 1. The obtained photoelectric conversion element was found to have an open end voltage of 770 mV, a short-circuit current density of 8.71 mA/cm$^2$, a fill factor of 0.58, and a photoelectric conversion efficiency of 3.90%, which showed good photoelectric conversion element performances thereof.

Example 2

Preparation of Photoelectric Conversion Element

A photoelectric conversion element was prepared in the same manner as in Example 1 except that diiodooctane was added to the solution for forming a photoelectric conversion layer so that a concentration thereof was 1% by mass.

Note that, an addition of a small amount of diiodooctane to the solution for forming a photoelectric conversion layer prevents an excessive aggregation, and can form an appropriate aggregated structure for charge separation and charge transportation.

<Evaluation>

Solar cell performances of the prepared photoelectric conversion element were measured upon irradiation of simulated solar light (AM1.5, 100 mW/cm$^2$) in the same manner as in Comparative Example 1. The obtained photoelectric conversion element was found to have an open end voltage of 720 mV, a short-circuit current density of 13.99 mA/cm$^2$, a fill factor of 0.53, and a photoelectric conversion efficiency of 5.38%, which showed good photoelectric conversion element performances thereof.

Example 3

Preparation of Photoelectric Conversion Element

A photoelectric conversion element was prepared in the same manner as in Example 1 except that a drying temperature for forming a photoelectric conversion layer was changed from 120° C. to room temperature (25° C.).

Note that, a degree of aggregation can be controlled by changing a drying temperature and by adjusting a drying time.

<Evaluation>

Solar cell performances of the prepared photoelectric conversion element were measured upon irradiation of simulated solar light (AM1.5, 100 mW/cm$^2$) in the same manner as in Comparative Example 1. The obtained photoelectric conversion element was found to have an open end voltage of 760 mV, a short-circuit current density of 10.79 mA/cm$^2$, a fill factor of 0.63, and a photoelectric conversion efficiency of 5.12%, which showed good photoelectric conversion element performances thereof.

Example 4

Preparation of Photoelectric Conversion Element

A glass substrate with a patterned ITO was subjected to ultrasonic washing and UV ozone cleaning. A solution of zinc oxide was coated on the substrate by a spin coating method, and then the resultant product was dried at 200° C. for 10 minutes, to thereby form a zinc oxide film having a thickness of 35 nm.

Next, an organic material shown in the Exemplary Compound 2 and PC71BM (phenyl C71 butyric acid methyl ester, product of Frontier Carbon Corporation) are dissolved in chloroform (1 mL) at a ratio of 7 mg:7 mg. Then, the resultant mixture was stirred overnight or longer in a glove box that had been purged with nitrogen, to thereby prepare a solution for forming a photoelectric conversion layer.

Then, the obtained solution for forming a photoelectric conversion layer was coated for film formation on the zinc oxide film in the atmosphere by a spin coating method, to thereby form a film thereon. Then, the film was dried at room temperature (25° C.), to thereby form a photoelectric conversion layer. The obtained photoelectric conversion layer was found to have an average thickness of 118 nm.

Next, using a vacuum evaporation method under 1×10$^{-6}$ Torr, a molybdenum oxide film was formed on the photoelectric conversion layer so that the thickness thereof was 10 nm, and an Ag electrode film was formed thereon so that the thickness thereof was 80 nm, to thereby form a photoelectric conversion element.

<Evaluation>

Solar cell performances of the prepared photoelectric conversion element were measured upon irradiation of simulated solar light (AM1.5, 100 mW/cm$^2$) in the same manner as in Comparative Example 1. The obtained photoelectric conversion element was found to have an open end voltage of 770 mV, a short-circuit current density of 9.03 mA/cm$^2$, a fill factor of 0.49, and a photoelectric conversion efficiency of 3.41%, which showed good photoelectric conversion element performances thereof.

Example 5

Preparation of Photoelectric Conversion Element

A photoelectric conversion element was prepared in the same manner as in Example 4 except that diiodooctane was added to the solution for forming a photoelectric conversion layer so that a concentration thereof was 1% by mass.

Note that, addition of a small amount of diiodooctane to the solution for forming a photoelectric conversion layer prevents excessive aggregation, and can form an appropriate aggregated structure for charge separation and charge transportation.

<Evaluation>

Solar cell performances of the prepared photoelectric conversion element were measured upon irradiation of simulated solar light (AM1.5, 100 mW/cm$^2$) in the same manner as in Comparative Example 1. The obtained photoelectric conversion element was found to have an open end voltage of 760 mV, a short-circuit current density of 12.15 mA/cm$^2$, a fill factor of 0.63, and a photoelectric conversion efficiency of 5.78%, which showed good photoelectric conversion element performances thereof.

Example 6

Preparation of Photoelectric Conversion Element

A photoelectric conversion element was prepared in the same manner as in Example 5 except that a drying temperature for forming a photoelectric conversion layer was changed from room temperature (25° C.) to 100° C.

Note that, a degree of aggregation can be controlled by changing a drying temperature and by adjusting a drying time.

<Evaluation>

Solar cell performances of the prepared photoelectric conversion element were measured upon irradiation of simulated solar light (AM1.5, 100 mW/cm$^2$) in the same manner as in Comparative Example 1. The obtained photoelectric conversion element was found to have an open end voltage of 700 mV, a short-circuit current density of 13.11 mA/cm$^2$, a fill factor of 0.56, and a photoelectric conversion efficiency of 5.16%, which showed good photoelectric conversion element performances thereof.

Comparative Example 2

Preparation of Photoelectric Conversion Element

A glass substrate with a patterned ITO was subjected to ultrasonic washing and UV ozone cleaning. A solution of polyethylene dioxythiophene:polystyrene sulfonic acid (product of H. C. Stark, Clevios P VP AI4083 was coated on the substrate by a spin coating method (speed of rotation: 3,000 rpm), and then the resultant product was dried at 130° C. for 10 minutes.

Next, Comparative Compound 1 represented by the following structural formula and PC71BM (phenyl C71 butyric acid methyl ester, product of Frontier Carbon Corporation) were dissolved in chloroform (1 mL) at a ratio of 15 mg:15 mg. Then, the resultant mixture was stirred overnight or longer in a glove box that had been purged with nitrogen, to thereby prepare a solution for forming a photoelectric conversion layer.

[Comprative Compound 1]

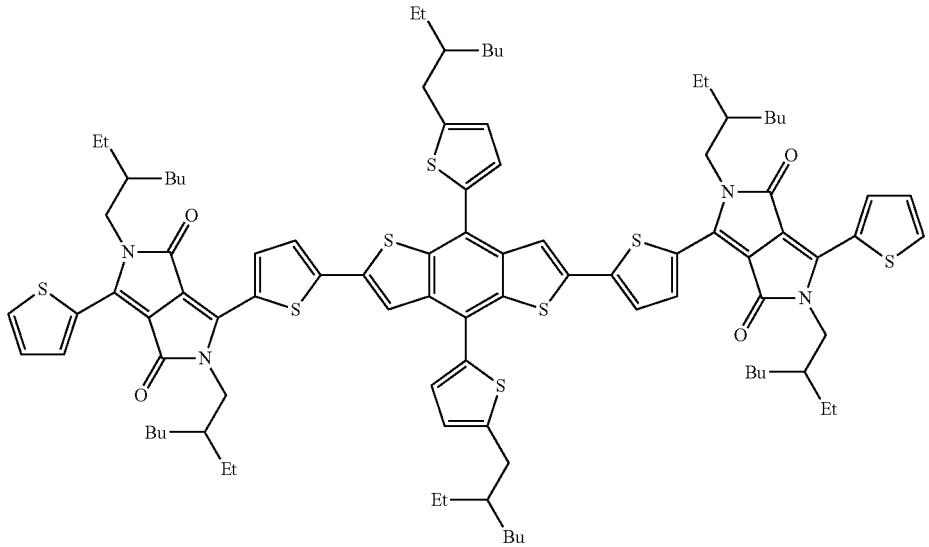

In the formula, where Et represents an ethyl group, and Bu represents a butyl group.

The Comparative Compound 1 was synthesized in the same manner as in the method described in ACS Applied Materials & Interfaces (2013), 5 (6), 2033-2039.

Then, the obtained solution for forming a photoelectric conversion layer was coated for film formation on the PEDOT:PSS film in the atmosphere by a spin coating method, to thereby form a photoelectric conversion layer. The obtained photoelectric conversion layer was found to have an average thickness of 180 nm.

Next, using a vacuum evaporation method under $1 \times 10^{-6}$ Torr, a Ca film was formed on the photoelectric conversion layer so that the thickness thereof was 3 nm, and an Al electrode film was formed thereon so that the thickness thereof was 80 nm, to thereby form a photoelectric conversion element.

<Evaluation>

Solar cell performances of the prepared photoelectric conversion element were measured upon irradiation of simulated solar light (AM1.5, 100 mW/cm$^2$) in the same manner as in Comparative Example 1. The obtained photoelectric conversion element was found to have an open end voltage of 840 mV, a short-circuit current density of 6.86 mA/cm$^2$, a fill factor of 0.43, and a photoelectric conversion efficiency of 2.43%.

Comparative Example 3

Preparation of Photoelectric Conversion Element

A photoelectric conversion element was prepared in the same manner as in Comparative Example 2 except that diiodooctane was added to the solution for forming a photoelectric conversion layer so that the concentration thereof was 0.3% by mass.

Note that, addition of a small amount of diiodooctane to the solution for forming a photoelectric conversion layer prevents an excessive aggregation, and can form an appropriate aggregated structure for charge separation and charge transportation.

<Evaluation>

Solar cell performances of the prepared photoelectric conversion element were measured upon irradiation of simulated solar light (AM1.5, 100 mW/cm$^2$). The obtained photoelectric conversion element was found to have an open end voltage of 760 mV, a short-circuit current density of 8.49 mA/cm$^2$, a fill factor of 0.60, and a photoelectric conversion efficiency of 3.88%.

Comparative Example 4

A photoelectric conversion element was prepared in the same manner as in Comparative Example 3 except that chloroform was changed to o-dichlorobenzene serving as a solvent in a solution for forming a photoelectric conversion layer and that the amount of diiodooctane was changed from 0.3% by mass to 0.7% by mass.

<Evaluation>

Solar cell performances of the prepared photoelectric conversion element were measured upon irradiation of simulated solar light (AM1.5, 100 mW/cm$^2$). The obtained photoelectric conversion element was found to have an open end voltage of 720 mV, a short-circuit current density of 9.23 mA/cm$^2$, a fill factor of 0.62, and a photoelectric conversion efficiency of 4.12%.

From the above results, photoelectric conversion elements of Examples 1 to 6 which were each prepared by using the organic material represented by the General Formula (1) exhibited higher photoelectric conversion efficiency compared with photoelectric conversion elements of Comparative Examples 1 to 4. Thus, it was found that the organic material represented by the General Formula (1) is sufficiently useful for materials for forming a photoelectric conversion element.

Aspects of the present invention are as follows, for example.

<1> An organic material represented by the following General Formula (1):

<General Formula (1)>

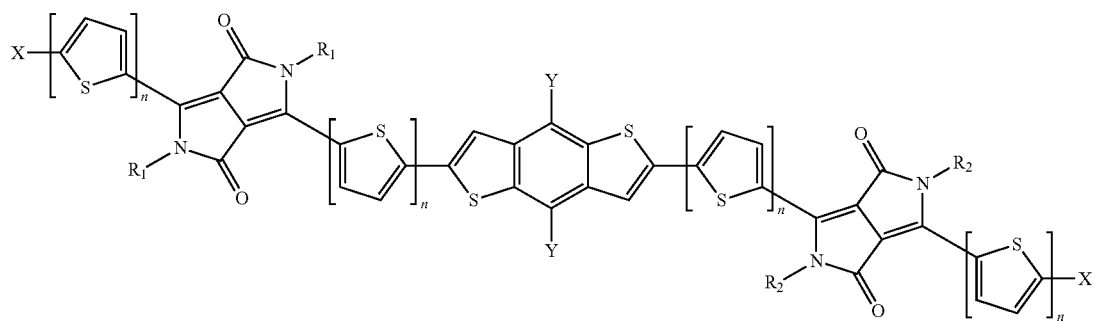

where in the General Formula (1), $R_1$ and $R_2$, which may be identical to or different from each other, each represent an alkyl group having 4 to 24 carbon atoms, X represents a substituted or unsubstituted aromatic hydrocarbon group, Y represents an aromatic hydrocarbon group, an alkoxyl group, or an alkyl group, which may be substituted with a substituent, and n represents an integer of 1 to 3.

<2> The organic material according to <1>, wherein Y is an aromatic hydrocarbon group.

<3> The organic material according to <1> or <2>, wherein n is 1.

<4> The organic material according to any one of <1> to <3>, wherein the organic material is represented by the following General Formula (2):

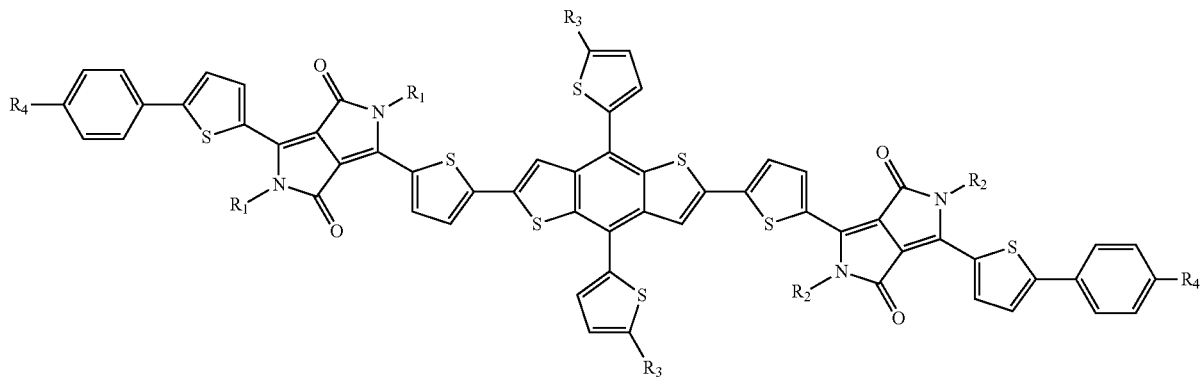

where in the General Formula (2), $R_1$ and $R_4$, which may be identical to or different from each other, each represent an alkyl group having 4 to 24 carbon atoms.

<5> A solution for forming a photoelectric conversion layer, including:
the organic material according to any one of <1> to <4>;
a n-type organic material; and
an organic solvent.

<6> The solution for forming a photoelectric conversion layer according to <5>, wherein the n-type organic material is a fullerene derivative.

<7> An organic material thin film, including:
the organic material according to any one of <1> to <4>; and
a n-type organic material.

<8> The organic material thin film according to <7>, wherein the n-type organic material is a fullerene derivative.

<9> A photoelectric conversion element, including:
an anode;
a cathode; and
the organic material thin film according to <7> or <8>, disposed between the anode and the cathode.

<10> The photoelectric conversion element according to <9>, wherein the anode is a transparent electrode.

<11> The photoelectric conversion element according to <9> or <10>, wherein the cathode is a transparent electrode.

This application claims priority to Japanese application No. 2014-075301, filed on Apr. 1, 2014 and incorporated herein by reference.

What is claimed is:

1. An organic material represented by the following General Formula (1):

<General Formula (1)>

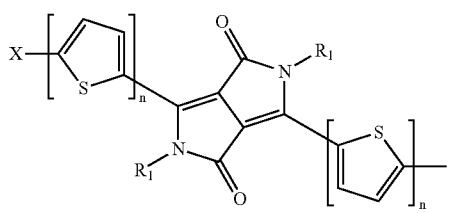

-continued

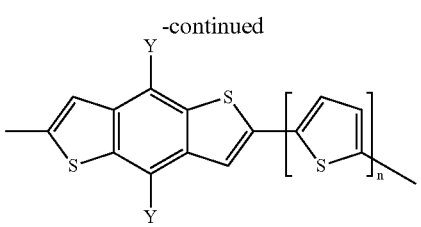

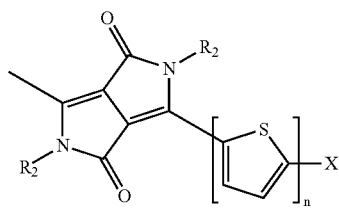

where in the General Formula (1), $R_1$ and $R_2$, which may be identical to or different from each other, each represent an alkyl group having 4 to 24 carbon atoms, X represents a substituted or unsubstituted aromatic hydrocarbon group, Y represents an aromatic hydrocarbon group, an alkoxyl group, or an alkyl group, which may be substituted with a substituent, and n represents an integer of 1 to 3.

2. The organic material according to claim 1, wherein Y is an aromatic hydrocarbon group.

3. The organic material according to claim 1, wherein n is 1.

4. The organic material according to claim 1, wherein the organic material is represented by the following General Formula (2):

<General Formula (2)>

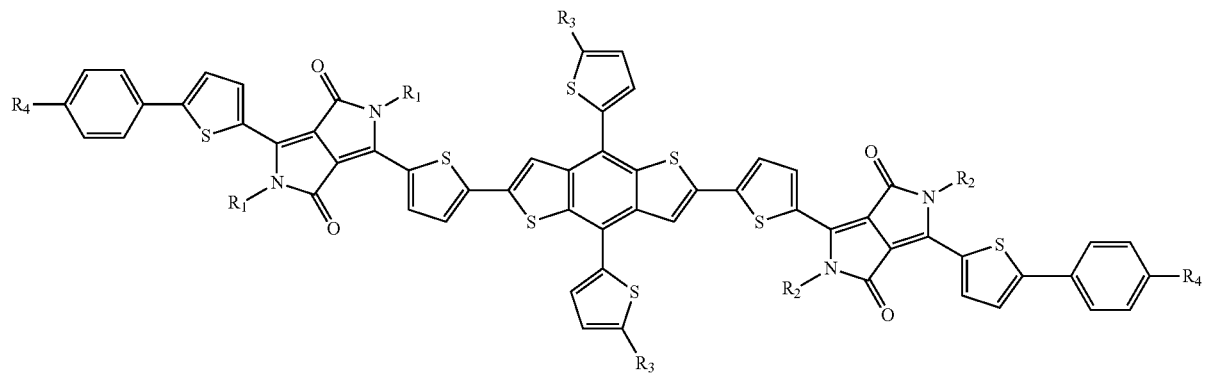

where in the General Formula (2), $R_1$ and $R_4$, which may be identical to or different from each other, each represent an alkyl group having 4 to 24 carbon atoms.

5. A solution for forming a photoelectric conversion layer, the solution comprising:
the organic material according to claim 1;
a n-type organic material; and
an organic solvent.

6. The solution for forming a photoelectric conversion layer according to claim 5, wherein the n-type organic material is a fullerene derivative.

7. An organic material thin film, comprising:
an organic material; and
a n-type organic material,
wherein the organic material is represented by the following General Formula (1):

an alkyl group having 4 to 24 carbon atoms, X represents a substituted or unsubstituted aromatic hydrocarbon group, Y represents an aromatic hydrocarbon group, an alkoxyl group, or an alkyl group, which may be substituted with a substituent, and n represents an integer of 1 to 3.

8. The organic material thin film according to claim 7, wherein the n-type organic material is a fullerene derivative.

9. A photoelectric conversion element, comprising:
an anode;
a cathode; and
an organic material thin film, disposed between the anode and the cathode,
wherein the organic material thin film contains an organic material and a n-type organic material,
wherein the organic material is represented by the following General Formula (1):

<General Formula (1)>

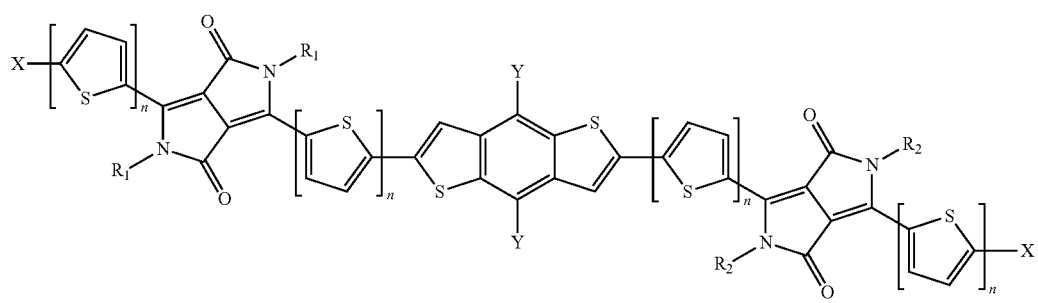

where in the General Formula (1), $R_1$ and $R_2$, which may be identical to or different from each other, each represent <General Formula (1)>

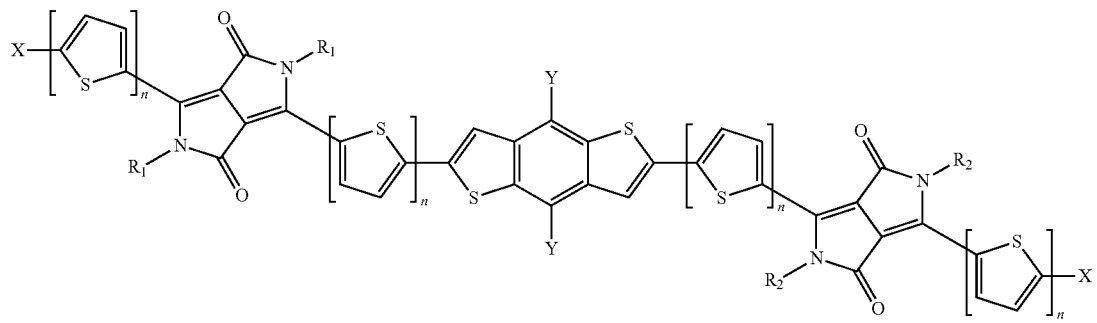

where in the General Formula (1), $R_1$ and $R_2$, which may be identical to or different from each other, each represent an alkyl group having 4 to 24 carbon atoms, X represents a substituted or unsubstituted aromatic hydrocarbon group, Y represents an aromatic hydrocarbon group, an alkoxyl group, or an alkyl group, which may be substituted with a substituent, and n represents an integer of 1 to 3.

10. The photoelectric conversion element according to claim 9, wherein the anode is a transparent electrode.

11. The photoelectric conversion element according to claim 9, wherein the cathode is a transparent electrode.

* * * * *